(12) United States Patent
Lee et al.

(10) Patent No.: US 12,350,336 B2
(45) Date of Patent: Jul. 8, 2025

(54) PHOTO-ACTIVATABLE COMPOUND, ITS PREPARATION AND THERAPEUTIC USE

(71) Applicant: City University of Hong Kong, Kowloon (HK)

(72) Inventors: Chun-Sing Lee, Kowloon (HK); Shengliang Li, Kowloon (HK); Yafang Xiao, Kowloon (HK); Wencheng Chen, Kowloon (HK)

(73) Assignee: City University of Hong Kong, Kowloon (HK)

( * ) Notice: Subject to any disclaimer, the term of this patent is extended or adjusted under 35 U.S.C. 154(b) by 67 days.

(21) Appl. No.: 17/589,943

(22) Filed: Feb. 1, 2022

(65) Prior Publication Data

US 2022/0241417 A1 Aug. 4, 2022

Related U.S. Application Data

(60) Provisional application No. 63/144,499, filed on Feb. 2, 2021.

(51) Int. Cl.
| | | |
|---|---|---|
| A61K 41/00 | (2020.01) | |
| A61K 9/51 | (2006.01) | |
| A61K 47/54 | (2017.01) | |

(52) U.S. Cl.
CPC ........ *A61K 41/0057* (2013.01); *A61K 9/5146* (2013.01); *A61K 47/545* (2017.08)

(58) Field of Classification Search
CPC .............. A61K 41/0057; A61K 9/5146; A61K 47/545; A61K 47/6909
See application file for complete search history.

(56) References Cited

PUBLICATIONS

Wen-Cheng, Charge-Transfer Complex, Adv. Funct. Mater. p. 1903112, Sep. 2019.*
Hu, DSPE-PEG2000 Complex with Doxorubicin, Bioconjug Chem. p.1 777, Jun. 2017.*
Lukyanov, Micelles from lipid derivatives, Adv. Drug Del. Rev. p. 1273, Dec. 2004.*
Kothavale, Donating group effects on fluorescence, Dyes and Pigments, June p. 209 (Year: 2018).*
Clinical development and potential of photothermal and photodynamic therapies for cancer Xingshu Li, Jonathan F. Lovell, Juyoung Yoon and Xiaoyuan Chen; Nature Reviews | Clinical Oncology.
Unimolecular Photodynamic O2-Economizer to Overcome Hypoxia Resistance in Phototherapeutics M. Li et al, | Journal of the American Chemical Society | J. Am. Chem. Soc. 2020, 142, 5380-5388.
Cancer-Cell-Activated in situ Synthesis of Mitochondria-Targeting AIE Photosensitizer for Precise Photodynamic Therapy | Y. Wang et al | Angew. Chem. 2021, 133, 15072-15080 T 2021 Wiley-VCH GmbH www.angewandte.de 15073.
Type 1 photodynamic therapy by organic-inorganic hybrid materials: form strategies to applications | Y. Wang et al | College of Chemistry, State Key Laboratory of Elemento-Organic Chemistry, Key Laboratory of Advanced Energy Materials (Ministry of Education), Nankai University , Tianjin 300071, China | Coordination Chemistry Reviews 395 (2019) 46-62.
Stable Organic Photosensitizer Nanoparticles with Absorption Peak beyond 800 Nanometers and High Reactive Oxygen Species Yield for Multimodality Phototheranostics | Y. Wan et al | ACS Publications | ACS Nano 2020 14, 9917-9928.
Dual-Mode Antibacterial Conjugated Polymer Nanoparticles for Photothermal and Photodynamic Therapy | H. Zhang et al | Advanced Science News | Macromolecular Bioscience | Macromol. Biosci. 2020, 20, 1900301.
Triple-functional albumin-based nanoparticles for combined chemotherapy and photodynamic therapy of pancreatic cancer with lymphatic metastases | X. Yu et al | International Journal of Nanomedicine—Sep. 12, 2017 | International Journal of Nanomedicine 2017:12 6771-6785.
Exploiting Tumour Hypoxia in Cancer Treatment J. Martin Brown et al | Nature Review | Cancer—vol. 4 | Jun. 2004 437-447.
A Bacteriochlorin-Based Metal-Organic Framework Nanosheet Superoxide Radical Generator for Photoacoustic Imaging-Guided Highly Efficient Photodynamic Therapy | K. Zhang et al | Adv. Sci. 2019, 6, 1900530; 1900530 (1 of 9); © 2019 The Authors. Published by Wiley-VCH Verlag Gmbh & Co. KGaA, Weinheim.
Superoxide Radical Photogenerator with Amplification Effect: Surmounting the Achilles' Heels of Photodynamic Oncotherapy | M. Li et al | ACS Publications | 10.1021/jacs.8b13141 | Am. Chem. Soc. 2019, 141, 2695-2702.
BODIPY-Based Photodynamic Agents for Exclusively Generating Superoxide Radical over Singlet Oxygen | K. Teng et al | Angew. Chem. Int. Ed. 2021, 60, 19912-19920.
Stable p-radical nanoparticles as versatile photosensitizers for effective hypoxia-overcoming photodynamic therapy | X. Cui et al | The Royal Society of Chemistry 2021 Mater. Horiz., 2021, 8, 571576 | 571.

(Continued)

*Primary Examiner* — Sarah Alawadi
*Assistant Examiner* — Thurman Wheeler
(74) *Attorney, Agent, or Firm* — Renner, Kenner, Greive, Bobak, Taylor & Weber

(57) ABSTRACT

A compound including a general formula of D-L-A particularly with the structure of Formula (A). A nanoparticle of the compound of the present invention. A pharmaceutical composition including the compound of the present invention as an active ingredient and a pharmaceutically acceptable carrier. A method of treating a target tissue including administering to a patient in need thereof a compound of the present invention and administering to the target tissue radiation in an amount and of a wavelength effective to activate the compound. Also use of the compound of the present invention in preparation of a medicament for treating the target tissue by photodynamic therapy.

11 Claims, 24 Drawing Sheets

(56) References Cited

PUBLICATIONS

Achieving high singlet-oxygen generation by applying the heavy-atom effect to thermally activated delayed fluorescent materials | Y. Xiao et al | Chem. Commun., 2021, 57, 4902-4905.

* cited by examiner

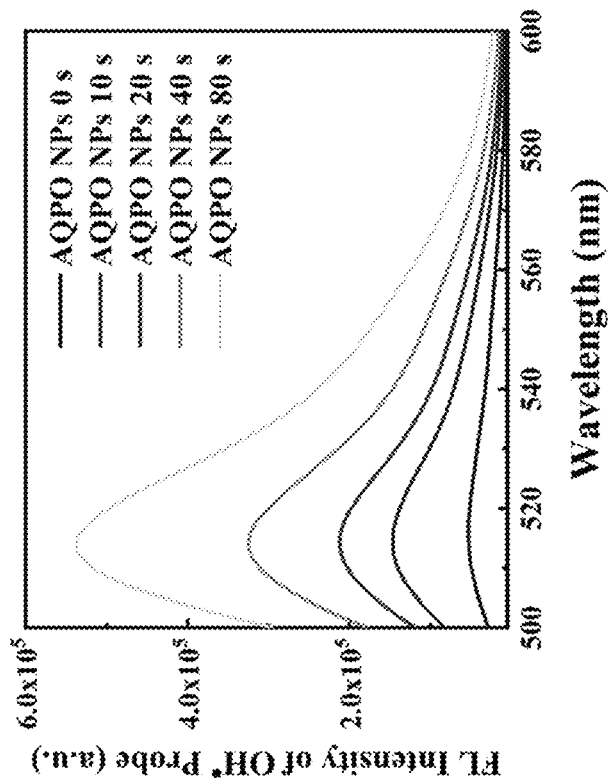
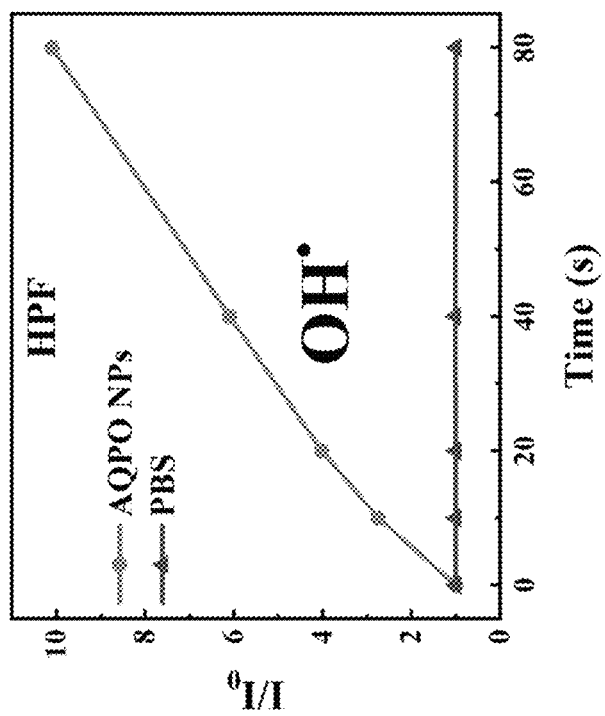
Fig. 12B
Fig. 12A

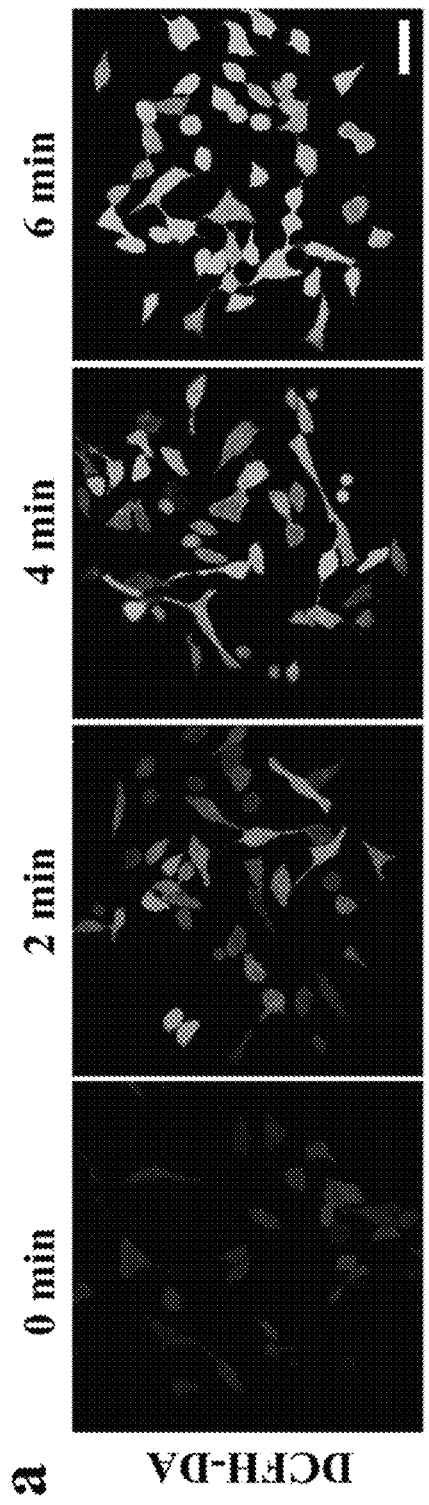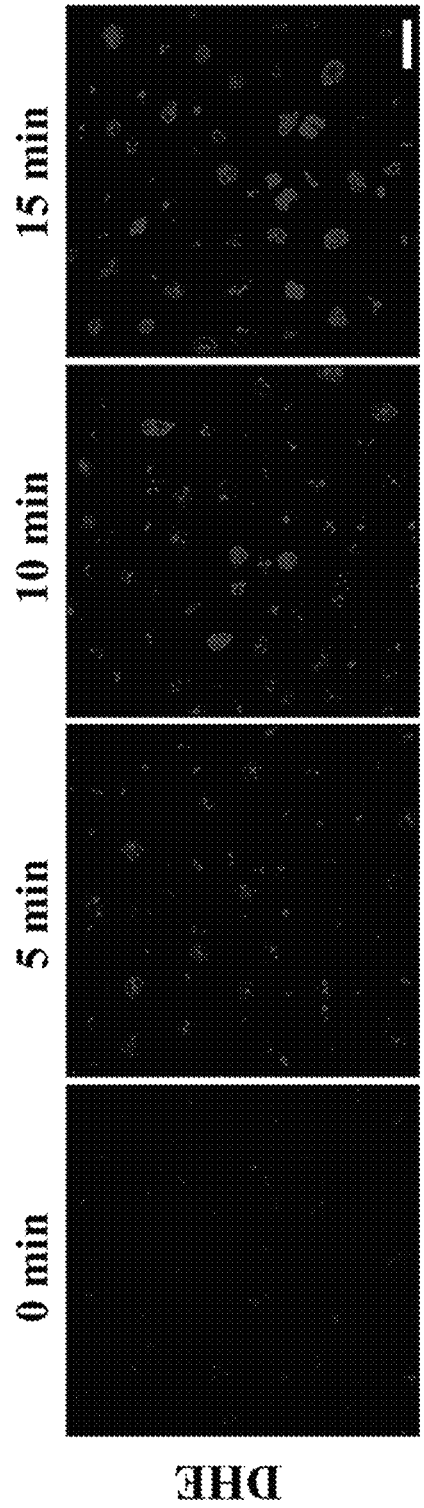

PHOTO-ACTIVATABLE COMPOUND, ITS PREPARATION AND THERAPEUTIC USE

FIELD OF THE INVENTION

The present invention is related to a novel compound in particular but not exclusive to a photo-activatable compound. The present invention also relates to the preparation of the compound as well as the use of it in treating a disease in particular but not exclusive to a cancer.

BACKGROUND

Cancer remains a life-threatening disease affecting a steadily increasing number of people overall in the world. Among various types of cancer treatments, photodynamic therapy (PDT) has been attracting much attention in treatment of various cancer diseases over the past decades because of its minimal invasion, low systemic toxicity, high spatiotemporal selectivity, and multidrug resistance-free characteristics. Typically, PDT involves exposing a photosensitizer (PS) to light with a specific wavelength range in conjunction with molecular oxygen to generate reactive oxygen species (ROS), which causes tumor cell apoptosis and/or necrosis. ROS generation can be generally classified into two distinct mechanisms, Type-I and Type-II processes.

As illustrated in FIG. 1, PS is excited from its ground state ($S_0$) to the singlet excited state ($S_1$) upon receiving photoirradiation within the specific wavelength. PS transits into triplet excited state ($T_1$) by exciton from the Si state ($^1PS*$) via intersystem crossing (ISC). In Type-I process, the $T_1$ excitons will interact with adjacent substrates and molecular oxygen to produce superoxide ($O_2^-\cdot$), peroxide ($O_2^-\cdot$), hydroxyl (OH$\cdot$) radicals or others. In Type-II process, singlet oxygen ($^1O_2$) is produced by triplet-triplet energy transfer between the $T_1$ excitation ($^3PS*$) and oxygen when $^3PS*$ decays back to the $S_0$ state.

Currently, the development of PSs, particularly organic PSs, mainly focuses on cyanine derivatives, boron-dipyrromethane (BODIPY) derivatives, porphyrin derivatives, chlorin or phthalocyanine derivatives, and aggregation-induced emission luminogens (AIEgens), etc. Most of these PSs produces $^1O_2$ via the Type-II process and such treatment is heavily dependent on $O_2$ concentration. However, in a typical solid tumor, its microenvironments is hypoxic ($pO_2$<5 mmHg) and therefore the dependent on $O_2$ concentration severely reduces the therapeutic effect of Type-II PSs in PDT. In addition, rapid $O_2$ consumption (owing to rapid metabolism) and vascular damage during the Type-II PDT further worsen the situation.

To increase the $O_2$ concentration inside solid tumor, reported methods includes hyperbaric oxygen therapy, delivering oxygen into tumors by oxygen shuttles, in situ oxygen generation by inorganic catalase. However, these methods often cause untoward side effects (e.g. hyperoxic seizures and barotrauma problem) or low treatment effect.

It has been reported that Type-I PSs can lower oxygen dependence by reducing consumption of $O_2$ in the PDT process. In particular, the formed $O_2^-\cdot$ species formed by the Type-I process not only serve as oxidants to kill tumor cells, but also participate in superoxide dismutase-triggered catalytic cascades to form highly cytotoxic OH$\cdot$ species and simultaneously produce $O_2$ for recycling. However, in most cases, such Type-I PDT is confined to some metal inorganic complexes with hindered clinical applications as they usually suffer from problems such as cytotoxicity in the dark, short-wavelength absorption, etc.

Thus, there remains a strong need for new organic PSs with not only Type-II but also Type-I ROS generation such that it can be effectively treating cancer in both hypoxic and normoxia microenvironments.

SUMMARY OF THE INVENTION

In a first aspect of the present invention, there is provided a compound comprising a general formula of:

$$D\text{-}L\text{-}A$$

wherein:
D is an electron donor comprising a structure of Formula (I):

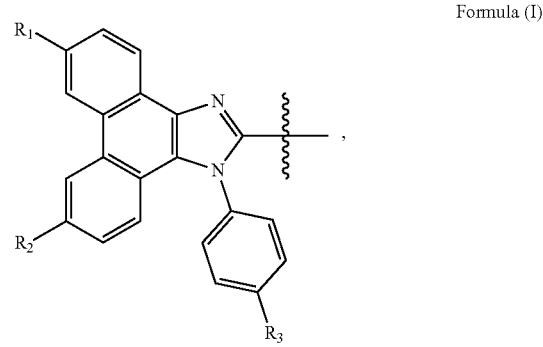

Formula (I)

and
with $R_1$, $R_2$, and $R_3$ being independently selected from a hydrogen atom, a substituted or unsubstituted linear or branched chain of alkyl group, an alkoxy group, or a substituted or unsubstituted aryl group;
L is a linker group comprising a substituted or unsubstituted phenyl group; and
A is an electron acceptor comprising an anthracene-9-10-dione moiety.

Preferably, $R_1$ and $R_2$, are independently selected from a hydrogen atom, or a substituted or unsubstituted phenyl group;
$R_3$ is selected from a hydrogen atom, a substituted or unsubstituted linear or branched chain of alkyl group, or an alkoxy group;
L is selected from any one of the following groups:

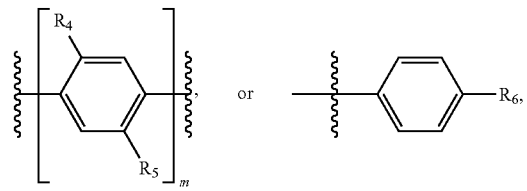

and
with $R_4$ and $R_5$ being independently selected from a hydrogen atom, a substituted or unsubstituted linear or branched chain of alkyl group, or an alkoxy group;
m being any positive integer;
$R_6$ being a secondary or a tertiary amide group, a secondary or a tertiary amino group, a saturated or unsaturated C1-C3 alkyl group unsubstituted or substituted with a aryl group; and A having a structure of Formula (II):

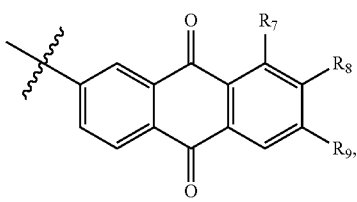

and with $R_7$, $R_8$, and $R_9$ each being independently a hydrogen or an adjacent pair of $R_7$, $R_8$, and $R_9$ may form a fused 6-membered carbocyclic ring.

It is preferred that $R_1$ and $R_2$ are independently selected from a hydrogen atom, a phenyl group, a phenyl-alkyl group, or a phenyl-alkoxy group;

$R_3$ is selected from a hydrogen atom or a C1-C3 alkoxy group;

L is selected from any one of the following groups:

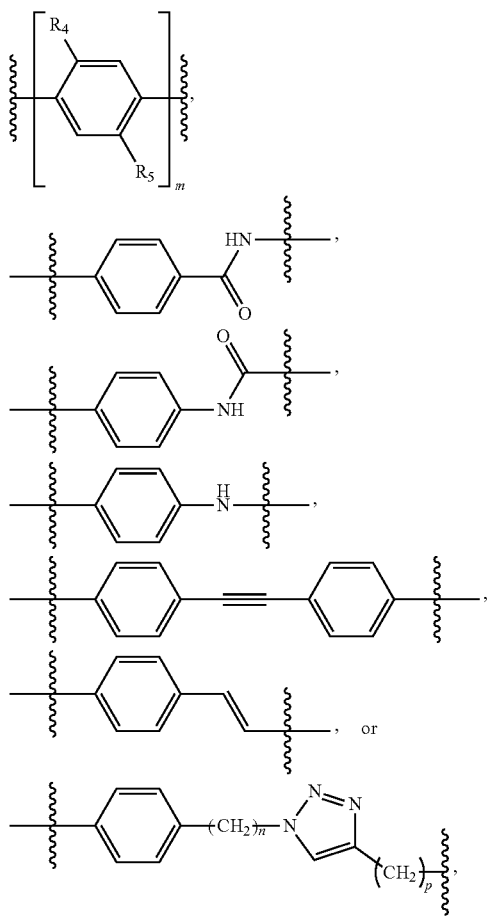

and with $R_4$ and $R_5$ being independently selected from a hydrogen atom, a linear or branched chain of C1-C4 alkyl group, or a C1-C3 alkoxy group;

m being 1, 2, or 3;

n and p are each independently being 1, 2, or 3; and

A has a structure of Formula (II), with $R_7$, $R_8$, and $R_9$ each being independently a hydrogen or an adjacent pair of $R_7$, $R_8$, and $R_9$ may form a unsubstituted phenyl ring.

In a preferred embodiment, the compound have a structure of Formula (III):

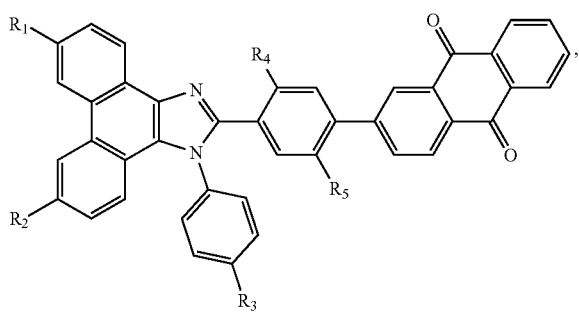

and with $R_1$ and $R_2$ being independently selected from any one of the following groups:

a hydrogen atom,

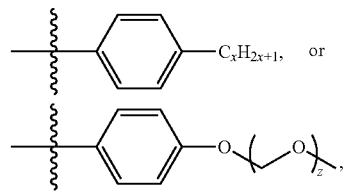

and with x and z each independently being 0 or any positive integer;

$R_3$ being a hydrogen atom, a methoxy, an ethoxy, or a propoxy group; and $R_4$ and $R_5$ are independently selected from a hydrogen atom, a methyl, an ethyl, a propyl, a tert-butyl, a methoxy, an ethoxy, or a propoxy group.

Preferably, $R_1$ and $R_2$ are identical and selected from any one of the following groups:

a hydrogen atom,

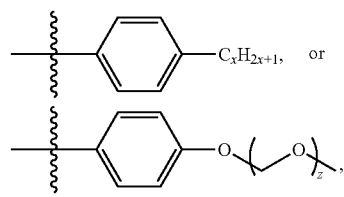

and with x and z each independently being 0, 1, 2, or 3;

$R_3$ being a hydrogen atom; and $R_4$ and $R_5$ are identical and being a hydrogen atom.

More preferably, the compound has a structure of Formula (IV), Formula (V), or Formula (VI):

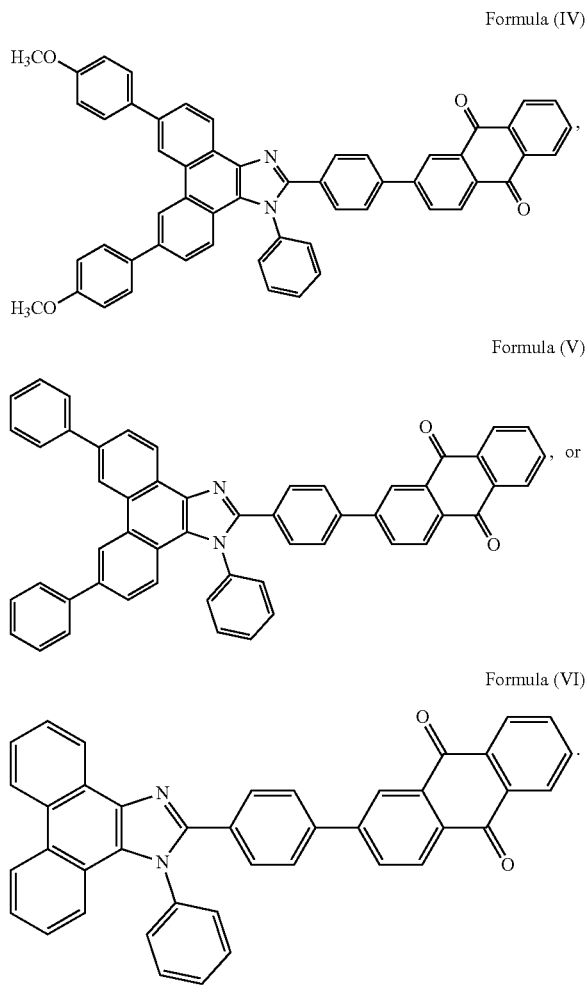

In a second aspect of the present invention, there is provided a method of preparing the compound in the first aspect, i.e. for preparing a compound comprising a structure of Formula

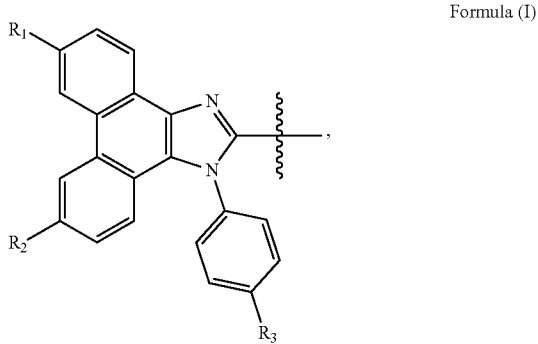

and with $R_1$, $R_2$, $R_3$, L, and A as described herein.

The present invention in a third aspect provides a pharmaceutical composition comprising a compound in the first aspect as an active ingredient and a pharmaceutically acceptable carrier.

According to a fourth aspect of the invention, there is provided a method of treating a target tissue, comprising administering to a patient in need thereof a compound according to the first aspect and administering to the target tissue radiation in an amount and of a wavelength effective to activate the compound. The radiation is light.

The light has a wavelength within visible spectrum. In a preferred embodiment, the light has a wavelength between about 400 nm to about 700 nm. The light is applied at a power intensity from about 0.5 mW/cm² to about 500 mW/cm². The target tissue is a tumor which may be cervical cancer, lung cancer, breast cancer, or mammary cancer.

In a preferred embodiment, the target issue is affected by an infection, in particular a bacteria infection, such as *Staphylococcus aureus* and/or *Escherichia coli* infection.

In a fifth aspect of the present invention, there is provided a use of the compound in the first aspect of the invention in preparation of a medicament for treating a target tissue by photodynamic therapy.

A sixth aspect of the invention pertains to a nanoparticle comprising a core in which the compound in the first aspect is disposed therein.

Preferably, the core comprises an amphiphilic polymer.

It is preferred that the amphiphilic polymer is selected from a group consisting DSPE-PEG2000, DSPE-PEG5000, Pluronic F-127, PLGA and a combination thereof In a preferred embodiment, the nanoparticle has an average particle size of about 25 nm to about 32 nm, preferably 29 nm.

BRIEF DESCRIPTION OF THE DRAWINGS

FIG. 12A shows a plot illustrating HPF activated rates of fluorescence by nanoparticle of Compound A of Formula (IV) prepared in an embodiment and PBS with the same area of integral absorption under white light irradiation (50 mW/cm$^2$). I and $I_0$ denote the fluorescence intensity of HPF at 514 nm before and after light irradiation, respectively.

FIG. 12B shows fluorescence spectra of HPF solutions with nanoparticle of Compound A of Formula (IV) prepared in an embodiment under the same area of integral absorption with Ce6 NPs for different irradiation time.

FIG. 14A shows fluorescence images of DCFH-DA with nanoparticle of Compound A of Formula (IV) prepared in an embodiment of the present invention in A549 cells after different irradiation times. Scale bar=30 μm.

FIG. 14B shows fluorescence images of DHE with nanoparticle of Compound A of Formula (IV) prepared in an embodiment of the present invention in A549 cells after different irradiation times. Scale bar=30 μm.

DESCRIPTION OF THE PREFERRED EMBODIMENTS

Figure 1:
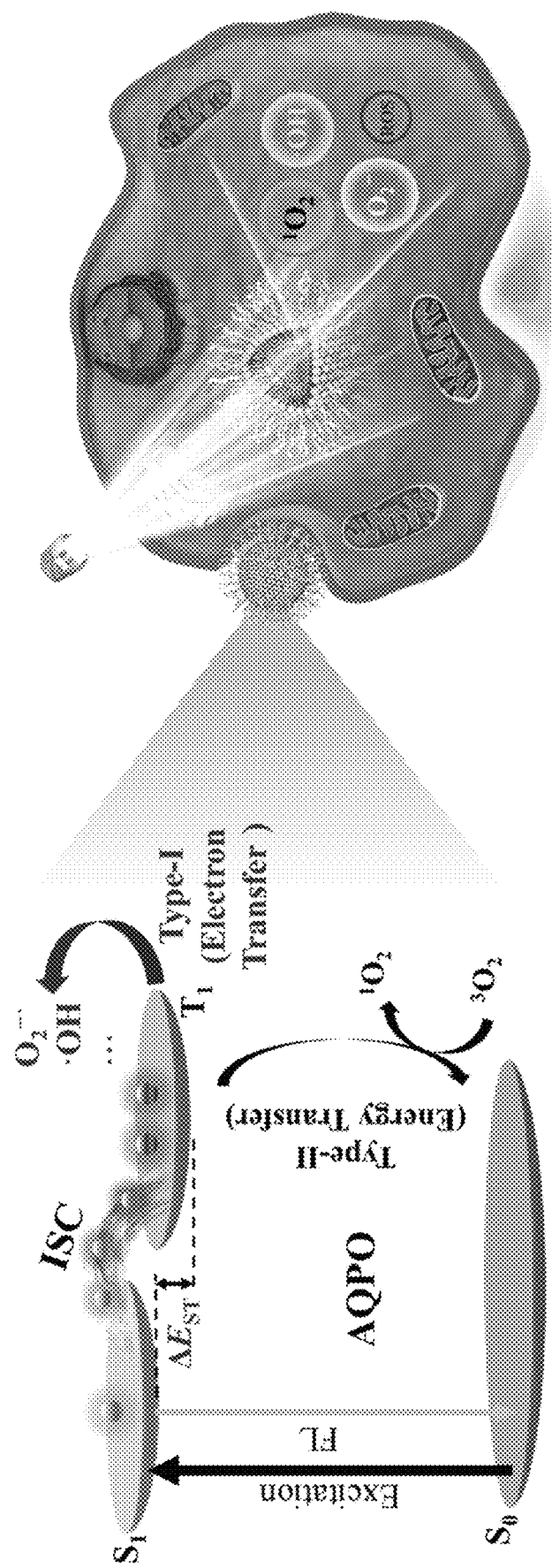
FIG. 1 shows a schematic diagram illustration of two photodynamic therapy (PDT) mechanisms and the multi-ROS response photosensitizer for hypoxia-overcoming PDT on cancer cells.

Unless otherwise specifically provided, all tests herein are conducted at standard conditions which include a room and testing temperature of 25° C., sea level (1 atm.) pressure, pH 7, and all measurements are made in metric units. Furthermore, all percentages, ratios, etc. herein are by weight, unless specifically indicated otherwise. It is understood that unless otherwise specifically noted, the materials compounds, chemicals, etc. described herein are typically commodity items and/or industry-standard items available from a variety of suppliers worldwide.

Unless otherwise defined, all technical terms used herein have the same meaning as commonly understood by one skilled in the art to which the invention belongs.

As used herein, the forms "a", "an", and "the" are intended to include the singular and plural forms unless the context clearly indicates otherwise.

The words "example" or "exemplary" used in this invention are intended to serve as an example, instance, or illustration. Any aspect or design described in this disclosure as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances.

Without intending to be limited by theory, the inventors have, through their own researches, trials, and experiments, devised that the compound as described herein may be used in photodynamic therapy (PDT). In particular, the compound may generate various reactive oxygen species (ROS) via both the Type-I and Type-II PDT mechanisms, including $^1O_2$, $O_2^-\cdot$, and OH. radicals, and therefore showing an excellent PDT performance in both cellular normoxia and hypoxia conditions. In an example embodiment, the compound as described herein may show a quantum yield of $^1O_2$ as high as about 18%. The compound may also produce about 12.6 times higher $O_2^-\cdot$ radical and about 3.8 times higher OH. as compared with an FDA-approved PDT compound, Chlorin e6 (Ce6).

According to the invention, there is provided a compound comprising a general formula of:

D-L-A wherein:
D is an electron donor comprising a structure of Formula (I):

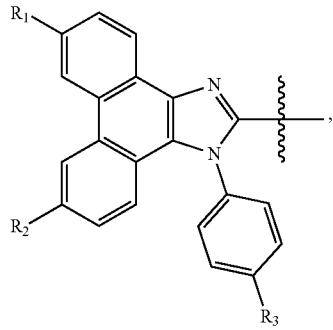

Formula (I)

and
with $R_1$, $R_2$, and $R_3$ being independently selected from a hydrogen atom, a substituted or unsubstituted linear or branched chain of alkyl group, an alkoxy group, or a substituted or unsubstituted aryl group;
L is a linker group comprising a substituted or unsubstituted phenyl group; and
A is an electron acceptor comprising an anthracene-9-10-dione moiety.

The compound of the present invention includes tautomers or geometric isomers, depending on the types of substituents. In the present description, the compound of the present invention is described only as a form of an isomer. However, the present invention also includes other isomers, and further, it includes separated isomers or a mixture thereof The compound is a photo-activatable compound. The phrase "photo-activatable" as used herein describes the compound to undergo photoexcitation and exhibit certain property only when exposed to a radiation. The compound may not exhibit such property or only exhibit such property to a negligible extent when it is not exposed to the radiation. In particular, the compound may be capable of generating/producing ROS such as but not limiting to $^1O_2$ upon photoexcitation. In the preferred embodiment, the compound undergoes photochemical reaction to generate or produce ROS such as $^1O_2$, $O_2^-\cdot$, OH. radicals and the like, preferably simultaneously.

The compound may include an electron donor D and an electron acceptor A linked/connected, by a linker group L. The electron donor D as used herein particularly refers to a photoelectron donor, which is a functional part of the compound with electron-donating ability upon photoexcitation. In particular, such functional part of the compound is capable of absorbing light at a given wavelength resulting in excitation of the compound from its ground state ($S_0$) to the singlet excited state ($S_1$), resulting in the excited compound ($^1Cpd^*$). Such functional part is also capable of interacting with the electron acceptor A such that a charge/electron is transferred to the electron acceptor A via intersystem crossing (ISC), turning the exciton in the $S_1$ state into the triplet excited state ($T_1$).

The electron donor of the compound is capable of absorbing light at a wavelength within the visible spectrum, in particular from about 400 nm to about 700 nm (i.e. white light).

$R_1$, $R_2$, and $R_3$ of the electron donor are independently selected from a hydrogen atom, a substituted or unsubstituted linear or branched chain of alkyl group, an alkoxy group, or a substituted or unsubstituted aryl group. The alkyl group can be saturated, straight-chain or branched hydrocarbons, which may, for example, contain between 1 and 20 carbon atoms such as 1 to 5, 1 to 4, or 1 to 3 carbon atoms. The alkoxy group can be saturated, straight-chain or branched hydrocarbons, which may, for example, contain between 1 and 20 carbon atoms such as 1 to 5, 1 to 4, or 1 to 3 carbon atoms, singularly bonded to an oxygen atom. The aryl group can be an aromatic monocyclic ring system having 6 ring atoms, including but not limiting to phenyl group, of which, all the ring atoms are carbon and which ring may be substituted with, for example, one or more of an alkyl group, an alkoxy group, and/or a halogen group such as bromide (Br) or chloride (Cl).

The electron acceptor A as used herein particularly refers to a photoelectron acceptor, i.e. a functional part of the compound with electron-withdrawing ability upon photoexcitation. In particular, such functional part of the compound is capable of interacting with the electron donor D via ISC, and receiving charge/(excited) electron therefrom, transiting the compound from $S_1$ state to $T_1$ state, with the generation of exciton in the $T_1$ state ($^3Cpd^*$). The electron acceptor as described herein is further capable of allowing the compound to generate ROS via both Type-I and Type-II mechanisms in subsequent photorelaxation processes. That being said, the electron acceptor can undergo a cascade of electron and/or proton transfer among the $T_1$ state, adjacent substrates and molecular oxygen to produce, including but not limiting to, $O_2^-\cdot$, OH. radicals and the like; and can undergo triplet-triplet energy transfer between the exciton in the $T_1$ state ($^3Cpd^*$) and oxygen when electron acceptor (and therefor the $^3Cpd^*$) decays back to the $S_0$ state, to produce $^1O_2$, i.e. the vertical $T_1 \rightarrow S_0$ emission energy of the electron acceptor is substantially the same as or larger than that required to excite $^3O_2$ to $^1O_2$. Preferably, the electron acceptor A may undergo both the Type-I and Type-II mechanisms simultaneously. The electron acceptor may be derived from an anthracene-9-10-dione moiety. In a particular embodiment, the electron acceptor may have a structure of Formula (II):

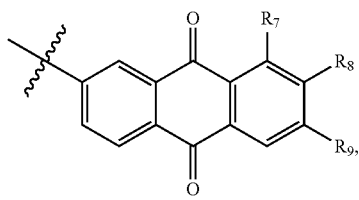

Formula (II)

and
with $R_7$, $R_8$, and $R_9$ each being independently a hydrogen or an adjacent pair of $R_7$, $R_8$, and $R_9$ may form a fused 6-membered carbocyclic ring, i.e. forming, for example, a phenyl ring and/or a cyclohexyl ring.

The linker group L is an organic unit of any lengths comprising atoms or groups to link, i.e. to connect, the electron donor and the electron acceptor of the compound of the present invention. Example includes substituted or unsubstituted phenyl group. In particular embodiments of the present invention, L is selected from any one of the following groups:

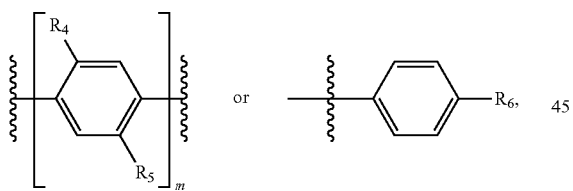

where $R_4$ and $R_5$ are independently selected from a hydrogen atom, a substituted or unsubstituted linear or branched chain of alkyl group, or an alkoxy group, and m is any positive integer such as 1, 2, or 3. $R_6$ is a secondary or a tertiary amide group, a secondary or a tertiary amino group, or a saturated or unsaturated C1-C3 alkyl group unsubstituted or substituted with an aryl group. As used herein, the phrase "secondary" describes the amide or the amino group having two organic substituents, such as an alkyl group, an acryl group or both, bound to the nitrogen together with one hydrogen. The phrase "tertiary" describes the amide or the amino group having three organic substituents bound to the nitrogen.

In an embodiment of the present invention, the compound of the present invention may have a structure of Formula (A):

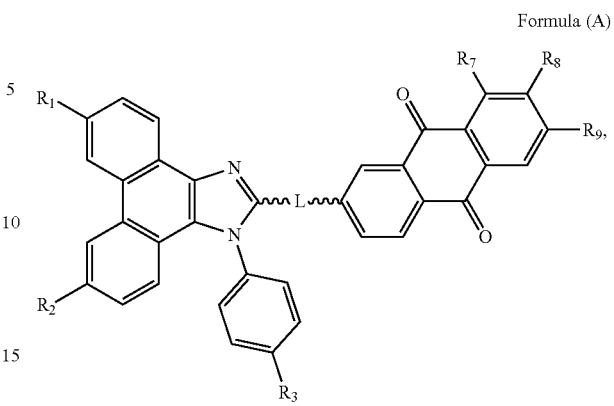

Formula (A)

where $R_1$ and $R_2$ are independently selected from a hydrogen atom, a phenyl group, a phenyl-alkyl group, or a phenyl-alkoxy group; $R_3$ is selected from a hydrogen atom or a C1-C3 alkoxy group; L is selected from any one of the following groups:

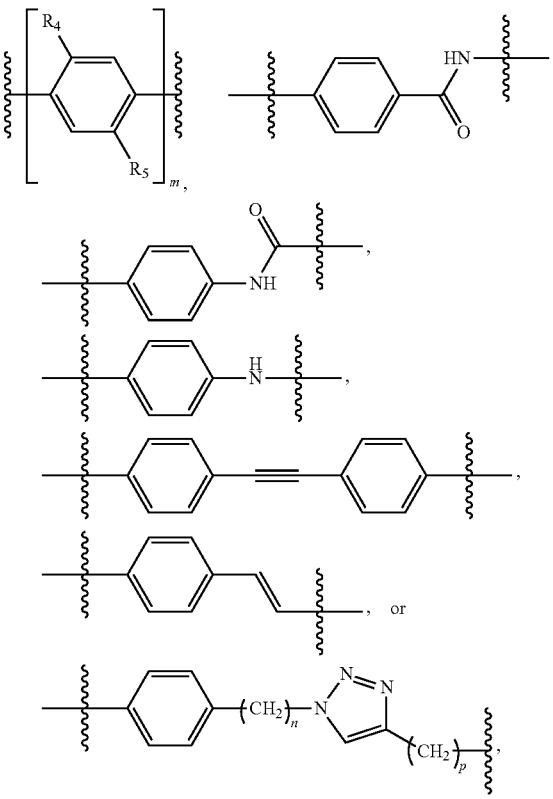

and
where $R_4$ and $R_5$ s are independently selected from a hydrogen atom, a linear or branched chain of C1-C4 alkyl group, or a C1-C3 alkoxy group; m is 1, 2, or 3; n and p are each independently being 1, 2, or 3; $R_7$, $R_5$, and $R_9$ each being independently a hydrogen or an adjacent pair of $R_7$, $R_8$, and $R_9$ may form a unsubstituted phenyl ring.

In an embodiment, the compound of the present invention may comprise a structure of Formula (III):

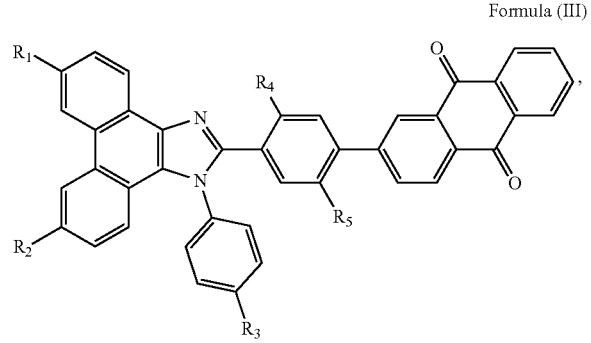

Formula (III)

and
with $R_1$ and $R_2$ being independently selected from any one of the following groups:
a hydrogen atom,

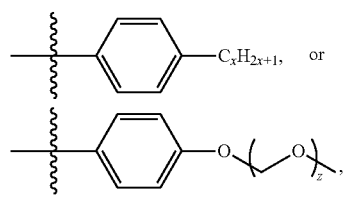

and
with x and z each independently being 0 or any positive integer such as 1, 2, 3, or 4;

$R_3$ being a hydrogen atom, a methoxy, an ethoxy, or a propoxy group; and $R_4$ and $R_5$ are independently selected from a hydrogen atom, a methyl, an ethyl, a propyl, a tert-butyl, a methoxy, an ethoxy, or a propoxy group.

In particular, $R_1$ and $R_2$ are identical and selected from any one of the following groups: a hydrogen atom,

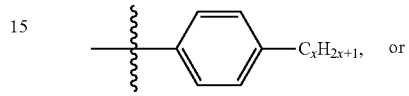

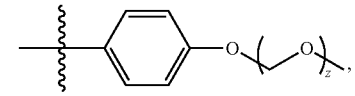

where x and z each independently being 0, 1, 2, or 3; $R_3$ being a hydrogen atom; and $R_4$ and $R_5$ are identical and being a hydrogen atom.

As specific embodiments, the compound of the present invention may have a structure of Formula (IV), Formula (V), or Formula (VI):

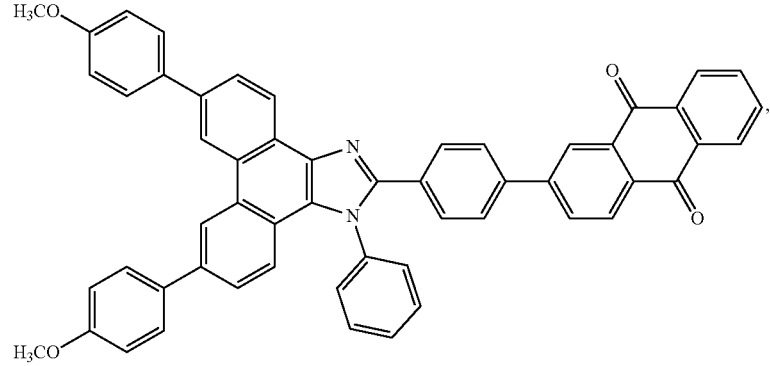

Formula (IV)

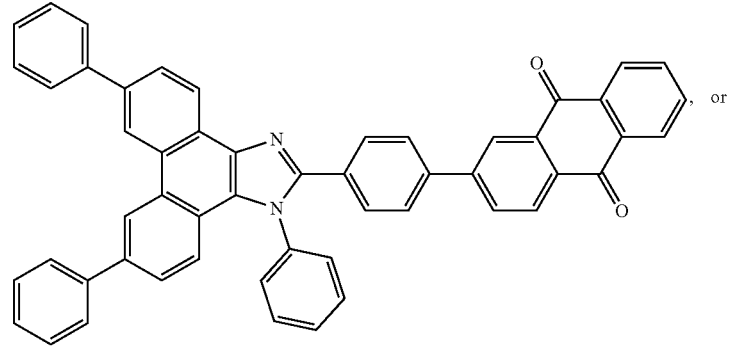

Formula (V)

-continued

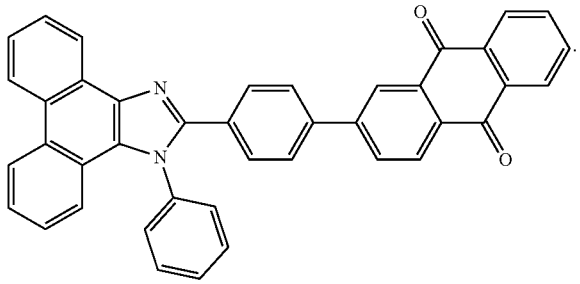

A method of preparing the compound is described below, i.e. for preparing a compound comprising the general formula of D-L-A with the structure of Formula (A):

Formula (A)

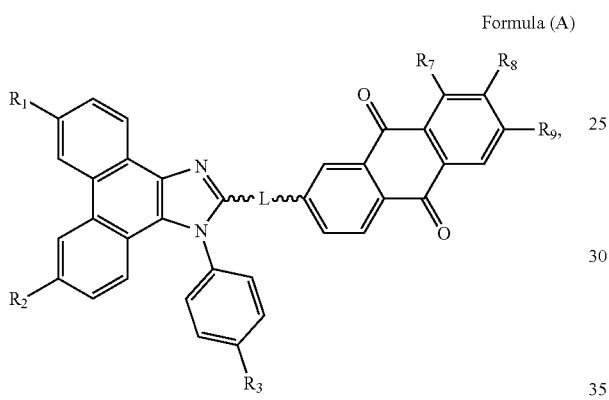

where $R_1$ and $R_2$ are independently selected from a hydrogen atom, a phenyl group, a phenyl-alkyl group, or a phenyl-alkoxy group; $R_3$ is selected from a hydrogen atom or a C1-C3 alkoxy group; L is selected from any one of the following groups:

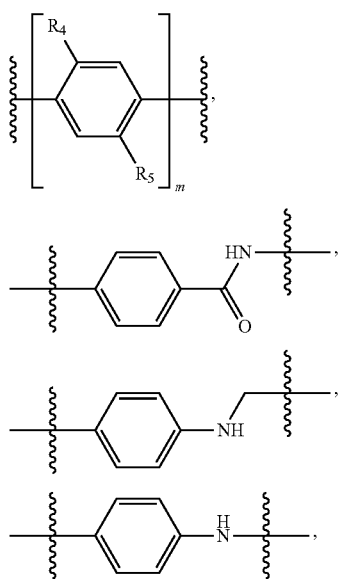

Formula (VI)

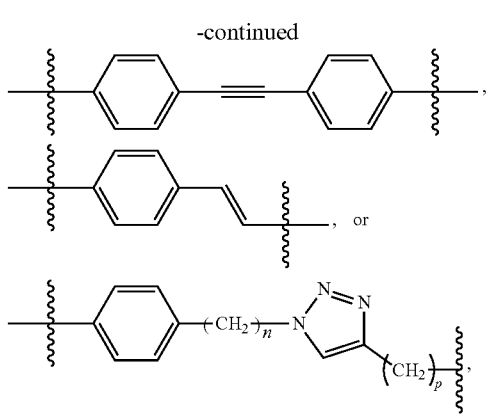

and where $R_4$ and $R_5$ are independently selected from a hydrogen atom, a linear or branched chain of C1-C4 alkyl group, or a C1-C3 alkoxy group; m is 1, 2, or 3; n and p are each independently being 1, 2, or 3; $R_7$, $R_8$, and $R_9$ each being independently a hydrogen or an adjacent pair of $R_7$, $R_8$, and $R_9$ may form an unsubstituted phenyl ring.

The method comprises linking a precursor compound which is a phenanthrene-9,10-dione compound with anthracene-9,10-dione moiety, i.e. a structure of Formula (II) as described herein via a linker group L as described herein, particularly the linker group selected from any one of the following groups:

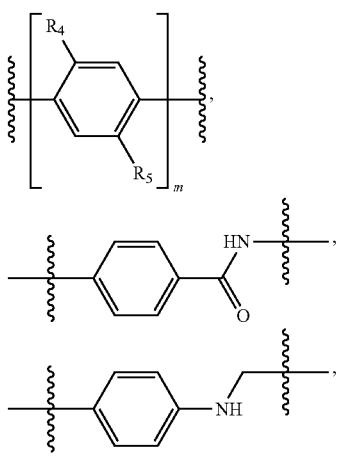

-continued

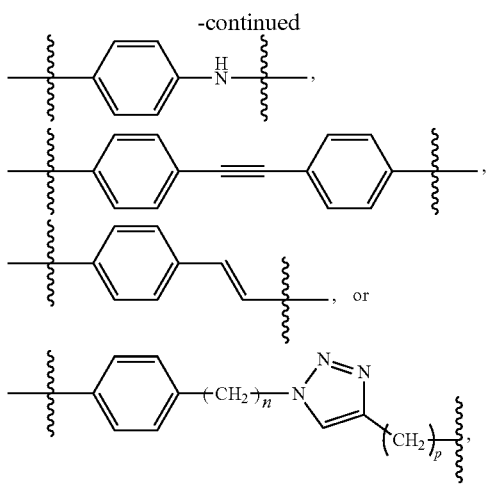

with $R_4$ and $R_5$, m, n, and p as defined herein.

The precursor compound may comprise a structure of Formula (VII):

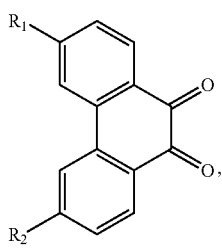

with $R_1$ and $R_2$ as defined herein.

The precursor compound may comprise a structure of Formula (VII), with $R_1$ and $R_2$ being independently selected from any one of the following groups:

a hydrogen atom,

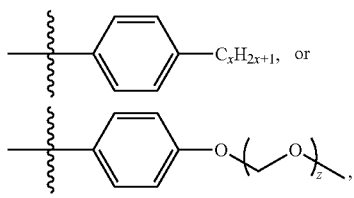

and with x and z each independently being 0 or any positive integer.

The precursor compound may comprise a structure of Formula (VII), with $R_1$ and $R_2$ being identical and selected from any one of the following groups:

a hydrogen atom,

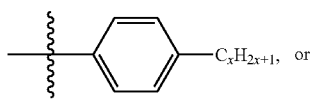

-continued

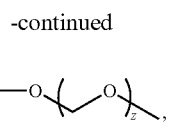

and with x and z each independently being 0, 1, 2, or 3.

The precursor compound may have a structure of Formula (VIII), Formula (IX), or Formula (X):

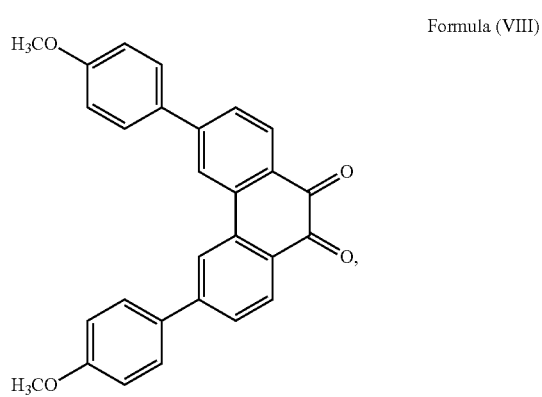

The method as described is suitable for preparing a compound of Formula (III):

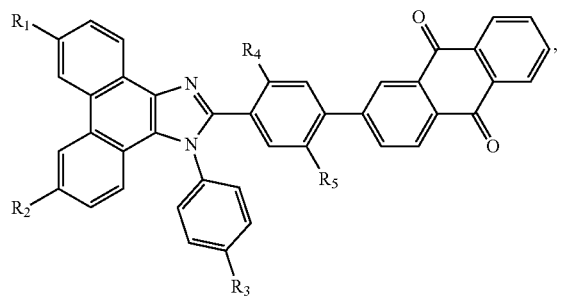

Formula (III)

where $R_1$ and $R_2$ are independent or preferably identical, and selected from any one of the following groups:

a hydrogen atom,

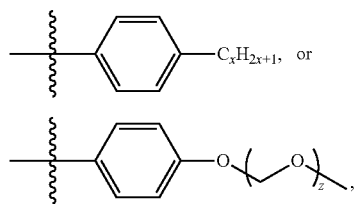

and with x and z each independently being 0 or any positive integer, preferably being 0, 1, 2, or 3;

$R_3$ being a hydrogen atom, a methoxy, an ethoxy, or a propoxy group, preferably being a hydrogen atom; and $R_4$ and $R_5$ are independently selected from a hydrogen atom, a methyl, an ethyl, a propyl, a tert-butyl, a methoxy, an ethoxy, or a propoxy group, in particular $R_4$ and $R_5$ are identical, or preferably $R_4$ and $R_5$ are identical and being a hydrogen atom.

The method comprises the steps of:
i) optionally preparing the precursor compound of Formula (VII), or in particular of Formula (VIII), or Formula (IX), from 3,6-dibromoohenanthrtene-9,10-dione;
ii) reacting the precursor compound, in particular of Formula (VIII), Formula (IX), or Formula (X), with linker precursors of Formula (XI) and Formula (XII), forming a compound of Formula (XIII):

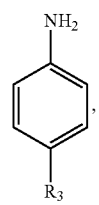

Formula (XI)

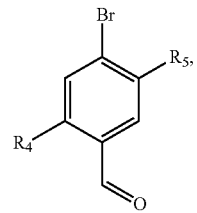

Formula (XII)

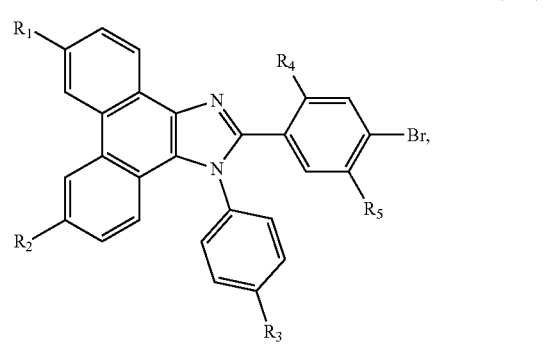

Formula (XIII)

with $R_1$ to $R_5$ as defined herein.
iii) converting the compound of Formula (XIII) into a dioxaborolane compound;
iv) reacting the dioxaborolane compound in step iii) with an anthracene-9,10-dione moiety having a structure of Formula (II), such as 2-bromoanthracene-9,10-dione; and
v) isolating the compound of Formula (III) and optionally purifying the compound.

Step i) in particular comprises the step of:
a) preparing a mixture of 3,6-dibromoohenanthrtene-9,10-dione, a boronic acid of Formula (XIV) and a palladium catalyst in a reaction solvent:

Formula (XIV)

and
with $R_{10}$ being

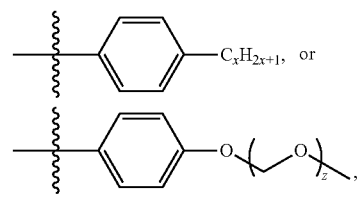

where x and z as defined herein; and
b) stirring the mixture after step a) for at least about 12 h at a temperature of about 90° C.

The molar ratio of 3,6-dibromoohenanthrtene-9,10-dione and the a boronic acid of Formula (XIV) may be from about 1:0.5 to about 1:5. The molar ratio of 3,6-dibromoohenanthrtene-9,10-dione and the palladium catalyst may be from about 50:1 to about 5:1.

Step ii) in particular comprises the steps of:
a) preparing a mixture of the precursor compound, in particular of Formula (VIII), Formula (IX), or Formula (X), with the linker precursors of Formula (XI) and Formula (XII) in a reaction solvent;
b) stirring the mixture after step a) for at least 24 h under reflux; and
c) isolating the compound of Formula (XIII) and optionally purifying the compound.

The reaction solvent in step iia) is particularly an acidic solution. Preferably, the acidic solution may be a glacial acetic acid solution. The molar ratio of the precursor compound and the two linker precursors may be from about 1:0.1:0.1:1 to about 1:5:5:50.

Step iii) in particular comprises the steps of:
a) preparing a mixture of compound of Formula (XIII), a palladium catalysts, potassium acetate, and bis(pinacolato)diboron; and
b) stirring the mixture after step a) for at least 24 h at a temperature from about 60° C. to about 150° C., or particular at about 95° C.

The molar ratio of the compound of Formula (XIII), bis(pinacolato)diboron, and potassium acetate may be from about 1:0.5:0.5 to about 1:5:5. The molar ratio of the compound of Formula (XIII) and the palladium catalyst may be from about 20:1 to about 10:1.

Step iv) in particular comprises the steps of:
a) preparing a mixture of the dioxaborolane compound obtained in step iii), the anthracene-9,10-dione moiety having a structure of Formula (II), such as 2-bromoanthracene-9,10-dione, and a palladium catalyst, in a reaction solvent, particularly an alkaline solution; and
b) stirring the mixture after step a) for at least 12 h at a temperature from about 60° C. to about 150° C., or particularly at about 90° C.

The molar ratio of the dioxaborolane compound obtained in step iii) and the anthracene-9,10-dione moiety may be from about 1:5 to about 1:0.5. The molar ratio of the dioxaborolane compound obtained in step iii) and the palladium catalyst may be from about 10:1 to about 50:1.

The alkaline solution as described above is preferably an alkaline solution prepared from alkali metal carbonate such as sodium carbonate, potassium carbonate, cesium carbonate and the like, with a concentration from about 0.5 M to about 5 M.

The palladium catalyst as described above may be selected from $Pd(PPh_3)_4$, $Pd(OAc)_2$ $Pd(TFA)_2$, $Pd(NO_3)_2$, $Pd(dppf)_2Cl_2$, and the combination thereof The expression "isolating" as used in the steps above means at least partially separating the compound as mentioned above from other components such as side products, the reactants and the solvent present in the reaction mixture in or after step (ii). The isolating step in particular may comprise filtering the mixture for obtaining a filtrate, extracting the crude (target) product with an extracting solvent such as chloroform, dichloromethane and the like, adding a precipitation solvent to the mixture such as methanol for obtaining a precipitate and washing the precipitate with a washing solvent such as methanol, cold water and the like.

The purification step as described above may be performed by column chromatograph such as silica-gel column chromatography, recrystallization or the like.

Preferably, the method is suitable for preparing a compound, in particular a photo-activatable compound comprising a structure of Formula (IV), Formula (V), or Formula (VI):

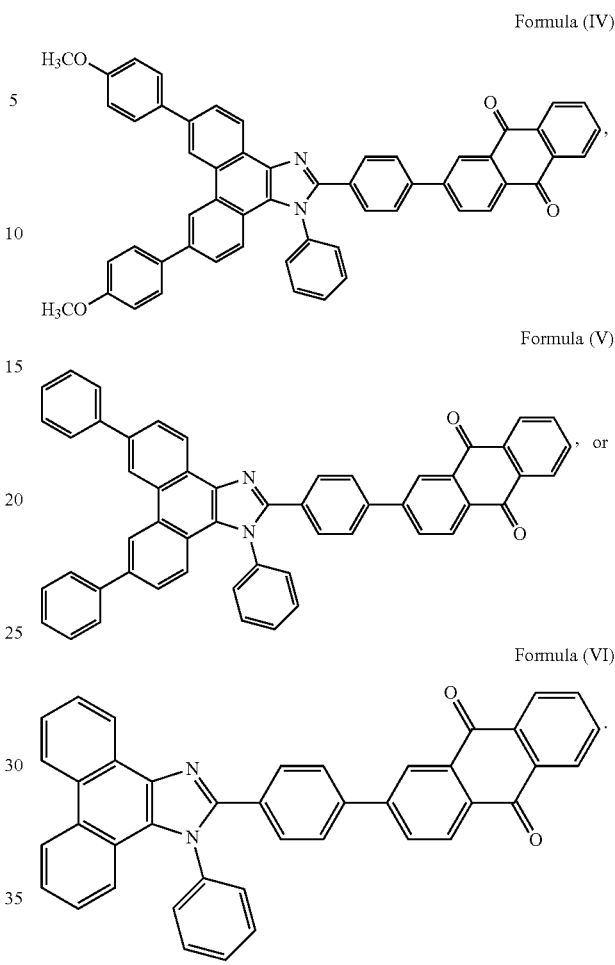

Another aspect of the invention relates to a pharmaceutical composition comprising a compound of the present invention as described herein as an active ingredient and a pharmaceutically acceptable carrier.

The compound in the pharmaceutical composition may comprise the general formula of D-L-A, particularly of a compound having a structure of Formula (A):

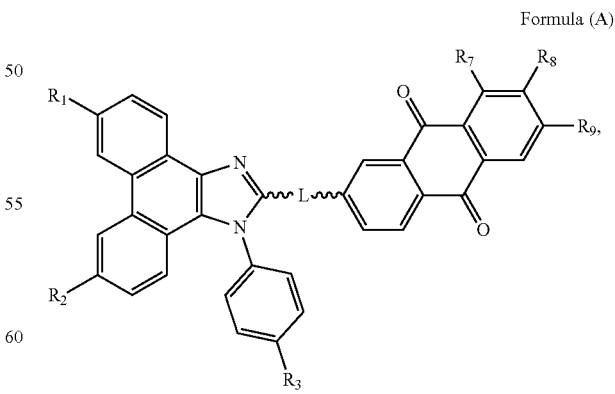

with $R_1$ to $R_3$, L, and $R_7$ to $R_9$ as defined herein.

In an embodiment of the present invention, the compound in the pharmaceutical composition may comprise a structure of Formula (III):

Formula (III)

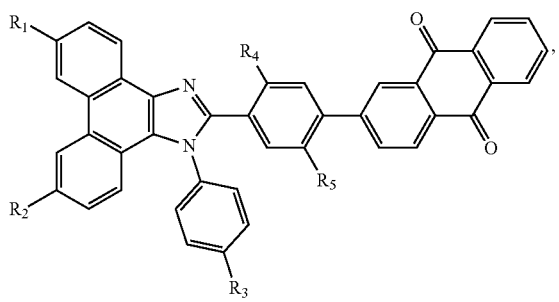

and with $R_1$ to $R_5$ as defined herein.

In particular, $R_1$ and $R_2$ may be independently selected from any one of the following groups:

a hydrogen atom,

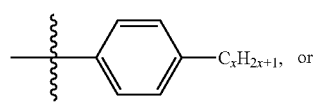

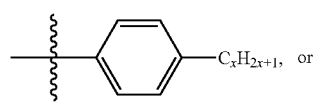

and with x and z each independently being 0 or any positive integer such as 1, 2, 3, or 4;

$R_3$ being a hydrogen atom, a methoxy, an ethoxy, or a propoxy group; and $R_4$ and $R_5$ are independently selected from a hydrogen atom, a methyl, an ethyl, a propyl, a tert-butyl, a methoxy, an ethoxy, or a propoxy group.

Preferably, $R_1$ and $R_2$ are identical and selected from any one of the following groups: a hydrogen atom,

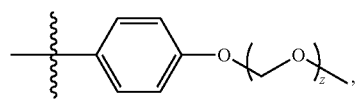

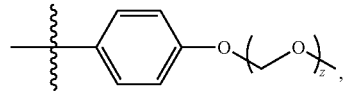

where x and z each
independently being 0, 1, 2, or 3; $R_3$ being a hydrogen atom; and $R_4$ and $R_6$ are identical and being a hydrogen atom.

More preferably, the compound may comprise a structure of Formula (IV), Formula (V), or Formula (VI):

Formula (IV)

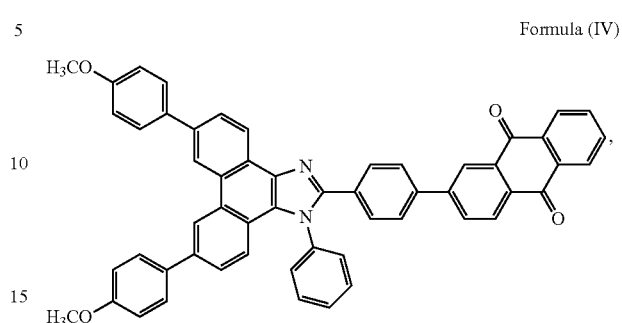

Formula (V)

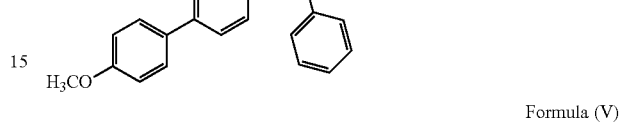

Formula (VI)

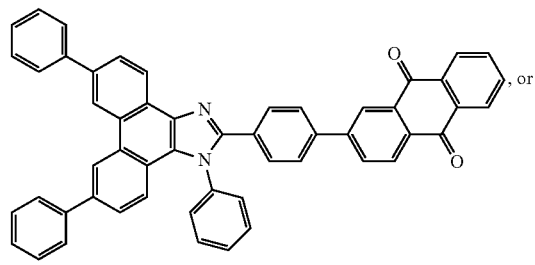

"Pharmaceutically acceptable carrier" are those that can facilitate the cellular uptake of the active ingredient and can be taken by a patient without therapeutically relevant adverse effects or negative influence in the efficiency of the compound. The pharmaceutical composition can be present in solid, semisolid or liquid form to be administered orally or via a parenteral route to the patient.

In an embodiment, the pharmaceutically acceptable carrier may be in form of nanoparticle, particularly a nanoparticle having a (nanoparticle) core which allows the compound of the present invention to be disposed and/or enclosed therein. The core of the nanoparticle may comprise an amphiphilic polymer. The term "amphiphilic polymer" as used herein generally denotes macromolecules that simultaneously contain hydrophobic and hydrophilic components. In particular, the hydrophobic component/part may form an inner layer enclosing the nanoparticle core, and the hydrophilic component/part may form an outer layer that interacts with the external environment such as a solvent. In other words, the nanoparticle may have a hydrophobic nanoparticle core defined by the hydrophobic component/part of the amphiphilic polymer, with a hydrophilic outer surface defined by the hydrophilic component/part of the amphiphilic polymer. This allows the nanoparticle and hence the compound of the present invention substantially dispersible in polar solvent or polar environment, such as but not limited to water, methanol and the like.

The amphiphilic polymer may be selected from DSPE-PEG2000, DSPE-PEG5000, Pluronic F-127, PLGA and a combination thereof. In a particular example embodiment, the amphiphilic polymer may be DSPE-PEG2000.

The nanoparticle may have a size from about 25 nm to about 32 nm, from about 25 nm to about 31 nm, from about 26 nm to about 31 nm, from about 26 nm to about 30 nm, from about 27 nm to about 30 nm, or in particular about 29 nm.

The present invention relates to a method of treating a target tissue, comprising administering to a patient the compound as described above and administering to the target tissue radiation in an amount and of a wavelength effective to activate the compound.

The term "target tissue" covers the site with cancer cells, cancerous tissues and any parts in proximity to the cancer cells or cancerous tissues, of a patient in need of treatment. The target tissue may be located topically or inside the body of the patient. After the step of administering the compound to the patient for a specific period of time, with the target tissue being pre-located, an effective amount of radiation with effective wavelength is applied to the target tissue for activating the compound that is at the site. (The electron donor D absorbs the radiation for excitation and subsequent photochemical reaction as detailed above).

In an embodiment, the target tissue may be a tumor, in particular being cancer. The term "tumor" or "tumorous" as referred herein describes an abnormal mass of tissue in a physiological condition in subjects (e.g. a patient), which may be benign, premalignant or malignant (cancerous) which may occurs in any part of the body of a patient including solid tissue such as organ, muscle, bone and the like.

The terms "cancer" and "cancerous" describe a physiological condition in subjects (e.g. a patient) in which a population of cells are characterized by unregulated malignant (cancerous) cell growth. The cancer may be or may not be a drug-resistant cancer. The expression "drug-resistant cancer" generally denotes a cancer which has a natural, i.e. intrinsic, or acquired resistance against one or more chemotherapeutic compounds in particular which has a natural or has an acquired, i.e. developed resistance against known coordination complexes of platinum such as cisplatin. A cancer is resistant against one or more chemotherapeutic compounds if it comprises cancer cells which are resistant against said chemotherapeutic compounds. Accordingly, the cancer cells with a resistant phenotype will be less sensitive or more tolerant to the one or more chemotherapeutic compounds. Such cancer or cancer cells can be detected for example, by means of an MTT assay.

In the preferred embodiment, the compound is used against malignant tumors in a patient who is diagnosed with cervical cancer, lung cancer, breast cancer, or mammary cancer.

In an alternative embodiment, the compound is used against target tissue that is affected by an infection, in particular by bacteria infection, such as but not limited to *Staphylococcus aureus* and *Escherichia coli* infection.

The administered compound has the general formula of D-L-A, particularly for a compound having a structure of Formula (A):

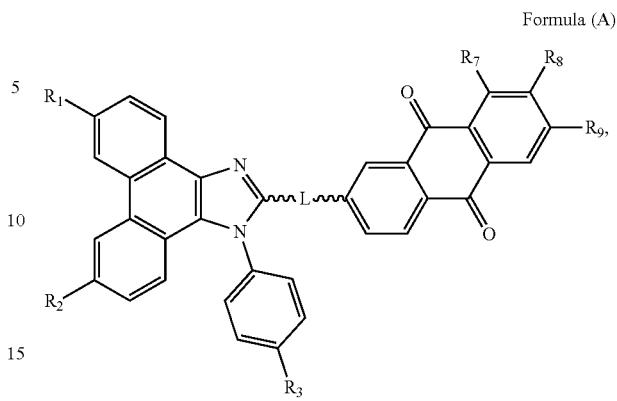

Formula (A)

with $R_1$ to $R_3$, L, and $R_7$ to $R_9$ as defined herein.

In an embodiment, the administrated compound may comprise a structure of Formula (III):

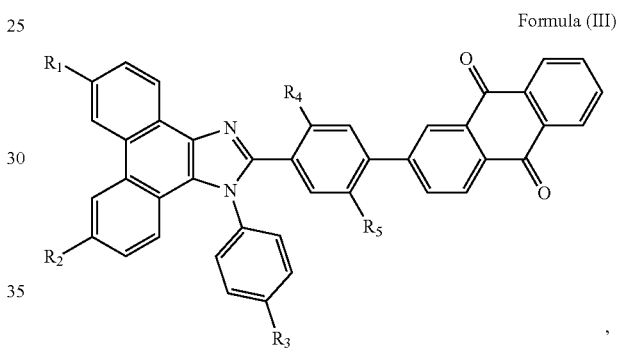

Formula (III)

and with $R_1$ to $R_5$ as defined herein.

In particular, $R_1$ and $R_2$ may be independently selected from any one of the following groups:

a hydrogen atom,

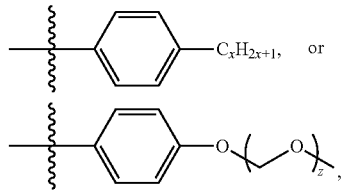

and with x and z each independently being 0 or any positive integer such as 1, 2, 3, or 4;

$R_3$ being a hydrogen atom, a methoxy, an ethoxy, or a propoxy group; and $R_4$ and $R_5$ are independently selected from a hydrogen atom, a methyl, an ethyl, a propyl, a tert-butyl, a methoxy, an ethoxy, or a propoxy group.

Preferably, $R_1$ and $R_2$ are identical and selected from any one of the following groups:

a hydrogen atom,

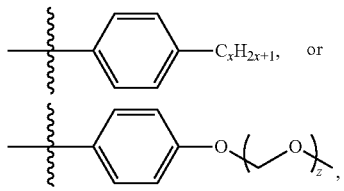

where x and z each independently being 0, 1, 2, or 3; $R_3$ being a hydrogen atom; and $R_4$ and $R_5$ are identical and being a hydrogen atom.

More preferably, the administered compound may comprise a structure of Formula (IV), Formula (V), or Formula (VI):

Formula (IV)

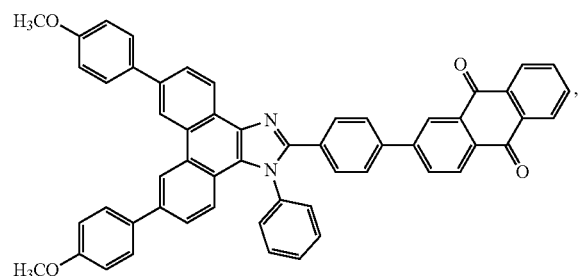

Formula (V)

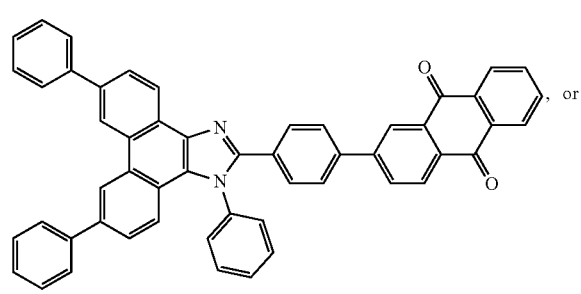

Formula (VI)

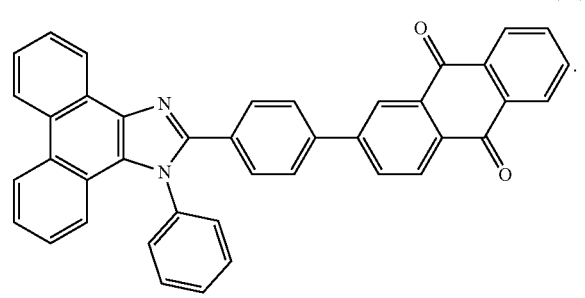

The amount of the compound to be administered depends on the species, body weight, age and individual conditions of the patient and can be determined by standard procedures such as with cell cultures or experimental animals. An effective amount or concentration of the compound is at least about 1 μg/mL.

The compound can be present in solid, semisolid or liquid form. In an embodiment of the invention, the compound is administered by an oral, topical or parenteral route to the subject, in particular by an oral route or an intravenous route.

The compound is prepared and administered in form of a pharmaceutical composition as described herein.

The term "radiation" as used herein may refer to electromagnetic (EM) radiation in particular EM radiation with a wavelength within the visible spectrum, i.e. visible light. The visible light administered to the patient may come from a natural source, such as by using apparatus to direct sunlight to the target tissue of the patient, or from an artificial source such as a visible light simulator that is configured to emit visible light to the patent at a particular power intensity and/or wavelength. Preferably, the radiation, which is visible light, may come from an artificial source.

The expressions "effective amount", "effective dose", and "effective wavelength" generally denote an amount of light or a particular range or specific wavelength sufficient to activate the compound of the present invention that is located in the target tissue, so as to produce therapeutically desirable results, wherein the exact nature of the result varies depending on the specific disorder which is treated. When the disorder involves a tumor, in particular cancer, the result is usually an inhibition or suppression of the proliferation of the cancer cells, a reduction of cancerous cells or the amelioration of symptoms related to the cancer cells. When the disorder is a bacterial infection, the result is the inhibition or suppression of the proliferation of the bacteria, a reduction of bacteria colony or the amelioration of symptoms related to the bacteria infection.

In particular, the "effective amount", "effective dose", and "effective wavelength" of the administered light may be sufficient and/or can be absorbed by the electron donor D of the compound for subsequent photochemical reaction as detailed above, allowing the compound to generate ROS, including $O_2^-·$, OH. radicals, and $^1O_2$ via both Type-I and Type-II mechanisms (i.e. activating the compound). The generated ROS may therefore act on the cancer cells, leading to at least an inhibition or suppression of the proliferation thereof As described herein, inhibiting the growth/proliferation of cancer cells (or bacteria) can mean a decrease in the cell (or bacteria) viability in particular a significant decrease and/or an increase in the number of apoptotic cells (or colony forming unit (CFU) for bacteria), in particular a significant increase. The skilled person is aware of methods for verifying such effects. For cancer cells, methods such as with cell viability measurement by means of a MTS proliferation assay, a MTT assay, a live/dead cell co-staining viability assay (Calcein-AM/PI), or by determination of the apoptosis rate by means of Annexin V flow cytometry measurement. For bacteria, standard colony counting method known in the art may be used, such as by means of determining bacteria inhibition rate (IR) using, for instance, Formula (1):

$$IR = \frac{C_0 - C}{C_0} \times 100\%, \quad \text{Formula (1)}$$

where C is the number of colony forming units (CFU) of the experimental group, and $C_0$ is the number of CFU of the control group.

As used herein, the term "significant" means that is statistically significant as determined by Student's t-test or other art-accepted measures of statistical significance.

The effect amount of administered light may be measured in terms of power intensity thereof. The power density may be from about 0.5 mW/cm$^2$ to about 500 mW/cm$^2$, from about 0.5 mW/cm$^2$ to about 450 mW/cm$^2$, from about 1 mW/cm$^2$ to about 500 mW/cm$^2$, from about 1 mW/cm$^2$ to about 400 mW/cm$^2$, from about 2 mW/cm$^2$ to about 300 mW/cm$^2$, from about 2 mW/cm$^2$ to about 200 mW/cm$^2$, from about 3 mW/cm$^2$ to about 250 mW/cm$^2$, from about 4 mW/cm$^2$ to about 100 mW/cm$^2$, from about 4 mW/cm$^2$ to about 80 mW/cm$^2$, or from about 5 mW/cm$^2$ to about 50 mW/cm$^2$. In an embodiment, the light is applied to the target area at a power density from about 30 mW/cm$^2$ to about 60 mW/cm$^2$, preferably about 50 mW/cm$^2$.

The effective wavelength of administered light is preferably within the visible spectrum. In particular, the wavelength may be from about 400 nm to about 700 nm (i.e. white light).

In a preferred embodiment or example of the invention, the compound has a structure of Formula (III), in particular of Formula (IV), Formula (V), or Formula (VI), the compound is capable of generating ROS, including $O_2^-\cdot$, OH. radicals, and $^1O_2$ via both Type-I and Type-II mechanisms, upon excitation of light with a wavelength from about 400 nm to about 700 nm.

That being said, the compound of the present invention, upon receiving light, may generate ROS including $O_2^-\cdot$, OH. radicals, and $^1O_2$ via both the oxygen-dependent pathway and oxygen-independent pathway, i.e. the generation of ROS by the compound of the present invention is substantially unaffected by cellular oxygen level. Accordingly, the compound of the present invention is particularly suitable for treatment of cancer as well as inhibition in cancer cells, of which the microenvironments is known to be hypoxic. The compound of the present invention is found to be effective in treating cancer under both normoxia and hypoxia upon excitation of light with a defined wavelength. In particular, the compound is found to have negligible difference of photocytotoxicity under normoxia and hypoxia conditions.

It is appreciated that, optionally or additionally, the method may be performed in combination with other therapeutically effective treatments such as one or more of:
i) treatment involving other therapeutically effective compounds such as chemotherapeutic compounds including, for example, a topoisomerase-II inhibitor, an anthracycline, a coordination complex of platinum, a taxane, a protein kinase inhibitor, a vinca alkaloid or derivative thereof, a topoisomerase-I inhibitor and a nucleotide analog or precursor analog;
ii) radiation therapy; and/or
iii) hormonal therapy.

The compound, in particularly the compound of Formula (III), Formula (IV), Formula (V) or Formula (VI) is suitable for or specifically designed for use as a medicament for the treatment of target tissue or is suitable for or specifically designed for use in the preparation of a medicament for treatment of the target tissue by photodynamic therapy as described herein. The target tissue may be a tumor, in particular a cancer as defined above. The target tissue may be affected by infection, in particular by bacteria infection, as defined above.

The medicament comprises the compound, in particularly the compound of Formula (III), Formula (IV), Formula (V) or Formula (VI) as described herein, and a pharmaceutically acceptable carrier as defined herein. In a particular embodiment, the pharmaceutical acceptable carrier may be in form of nanoparticle as defined herein.

The medicament may be of various forms, such as in oral or in injection form, depending on the administration method and using various conventionally used methods for preparing a medicament. Examples of oral formulations may include tablets, powders, granules, capsules, pills, lozenges, solutions, syrups, elixirs, emulsions, oily or aqueous suspensions, and so forth.

Examples of solid formulations include tablets, powders, granules, capsules, pills, and lozenges. These solid formulations may contain pharmaceutically acceptable additives together with a crystal of the present invention. Examples of additives include fillers, extenders, binders, disintegrating agents, dissolution promoting agents, skin wetting agents, and lubricants, and these can be selected and mixed as required to prepare a medicament.

Examples of liquid formulations include solutions, syrups, elixirs, emulsions, and suspensions. These liquid formulations may contain pharmaceutically acceptable additives together with a crystal of the present invention. Examples of additives include suspending agents and emulsifiers, and these are selected and mixed as required to prepare a formulation.

In another aspect, the invention provides a nanoparticle of the compound of the present invention comprising a core in which the compound is disposed therein, i.e. a nanoparticle having a core in which a compound in particular of Formula (A), preferably of Formula (III), Formula (IV), Formula (V), or Formula (VI) as defined herein is disposed/enclosed therein.

In an embodiment, the core of the nanoparticle may comprise an amphiphilic polymer as defined herein. In particular, the hydrophobic component/part of may form an inner layer enclosing the nanoparticle core, and the hydrophilic component/part may form an outer layer that may interact with the external environment such as a solvent. In other words, the nanoparticle may have a hydrophobic nanoparticle core defined by the hydrophobic component/part of the amphiphilic polymer, with a hydrophilic outer surface defined by the hydrophilic component/part of the amphiphilic polymer, which therefore may render the nanoparticle and therefore the compound of the present invention substantially dispersible in polar solvent or polar environment, such as but not limited to water, methanol and the like.

The amphiphilic polymer may be selected from DSPE-PEG2000, DSPE-PEG5000, Pluronic F-127, PLGA and a combination thereof. In a particularly example embodiment, the amphiphilic polymer may be DSPE-PEG2000.

The nanoparticle may have a size from about 25 nm to about 32 nm, from about 25 nm to about 31 nm, from about 26 nm to about 31 nm, from about 26 nm to about 30 nm, from about 27 nm to about 30 nm, or in particular about 29 nm.

A method of preparing the nanoparticle is described herein. The method may comprise the steps of:
i) preparing a mixture of the compound as described herein and an amphiphilic polymer; and
ii) isolating the nanoparticle and optionally purifying the nanoparticle.

Step i) in particular may comprise:
a) dissolving the compound and the amphiphilic polymer, respectively, in an organic solvent, such as ethanol, tetrahydrofuran, dimethylsulfoxide (DMSO), dimethylformamide (DMF) and the like;
b) adding the mixture dropwise into a reaction solvent such as water, in particular DI water, or a buffer such as 1× phosphate buffered saline (PBS); and c) stirring the mixture at a defined rpm, such as at least 1200 rpm, and optionally or additionally under ultra-sonication, for such as about 0.1 h to about 48 h, in particular for at least 1 h at room temperature (i.e. about 25° C.).

Step ii) in particular may comprise removing at least part of the organic solvent from the mixture by, for example, rotary evaporation, and subjecting the mixture to centrifugation. The purification may be performed by column chromatograph in particular size-exclusion chromatography with a defined molecular weight cut-off (MWCO), such as about 100,000. A person skilled in the art would recognize to vary the MWCO according to their practical need.

EXAMPLES

Materials and Reagents Used

All materials were purchased from commercial sources and used as received. DSPE-PEG2000, Dihydrorhodamine 123, Hydroxyphenyl fluorescein, 5,5-Dimethyl-1-pyrroline N-oxide, 2,2,6,6-Tetramethylpiperidine, Hoechst 33342, 3-(4,5-dimethyl-2-thiazolyl)-2,5-diphenyl-2-H-tetrazolium bromide (MTT), Calcein acetoxymethyl ester (Calcein-AM) and Propidium Iodide (PI) were purchased from Sigma-Aldrich. Multicolor Cell-Labeling Kit (DiO and DiD), 2',7'-dichlorodihydrofluorescein diacetate, Dihydroethidium, Dulbecco's Modified Eagle Medium (DMEM), 1× Phosphate-Buffered Saline (PBS, pH 7.4), Penicillin-Streptomycin (10,000 U/mL), Fetal Bovine Serum (FBS), and Trypsin-EDTA (0.5%, no phenol red) were purchased from Thermo Fisher Scientific.

Instrumentation and Characterization

Nuclear magnetic reasonance (NMR) spectra were recorded in $CDCl_3$ using a Bruker Advance-600 spectrometer, and mass spectra data were collected via Bruker autoflex MALDI-TOF mass spectrometer. Fluorescence spectra were measured using a Spectrofluorometer Fluormax-4 (HORIBA Jobin Yvon Inc.). Transient PL decay was measured using a spectrofluorometer of FLS980 (Edinburgh, UK). UV-Vis absorption spectra were recorded using an Ultra-Violet Visible Scanning Spectrophotometer Shimadzu 1700. Transmission electron microscopy (TEM) images were observed using an FEI/Philips Tecnai 12 BioTWIN. Electron spin resonance (ESR) spectra were obtained using a JEOL-FA200, Japan. DLS analysis measurements were recorded using a Dynamic Light Scattering Particle Size Analyzer (Malvern Zetasizer Nano ZS). Fluorescence images of the cells were taken using a Confocal Laser Scanning Microscope (Leica SPE).

All the calculations were performed using Gaussian 09 program package. The ground state geometries were optimized via density functional theory (DFT) at the B3LYP/6-31G* level. Time-dependent DFT (TD-DFT) with B3LYP method for energies were then performed in lowest-lying singlet ($S_1$) and triplet states ($T_1$) according to the geometry optimization.

Error bars denoted in any of the figures or values were based on standard error of mean (SEM) and n=3 or 5. The data are given as Mean±SEM.

Example 1A

Preparation of Compound A

Compound A of the present invention (i.e. compound of Formula (IV) of the present invention, AQPO) was generally prepared by reacting 6,9-bis(4-methoxyphenyl)-1,2-diphenyl-1H-phenanthro[9,10-d] imidazole as a donor and anthracene-9,10-dione as an acceptor through a Suzuki cross-coupling reaction. In particular, the preparation was performed according to Reaction scheme 1:

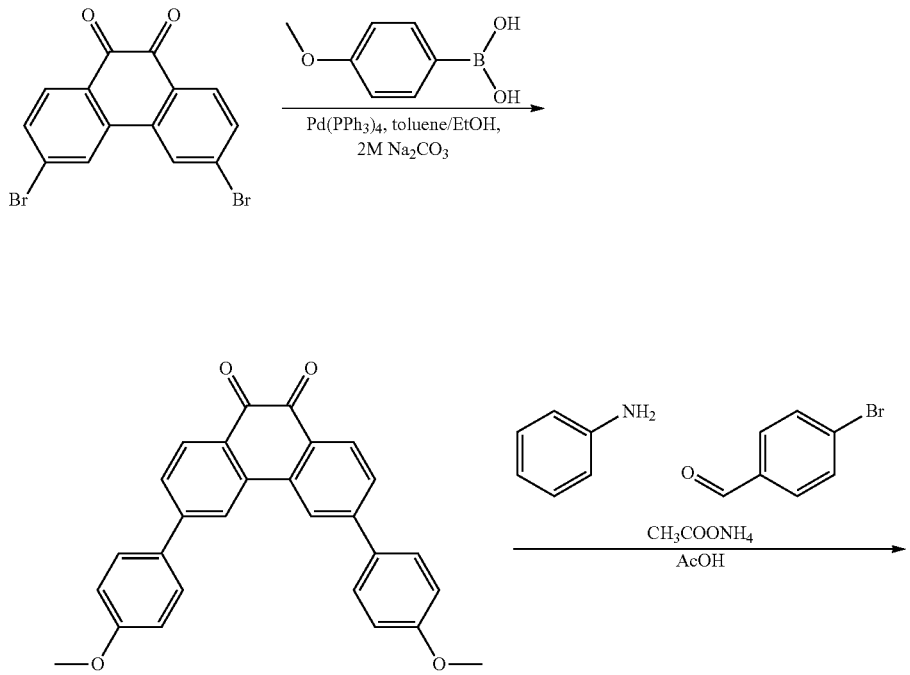

C1

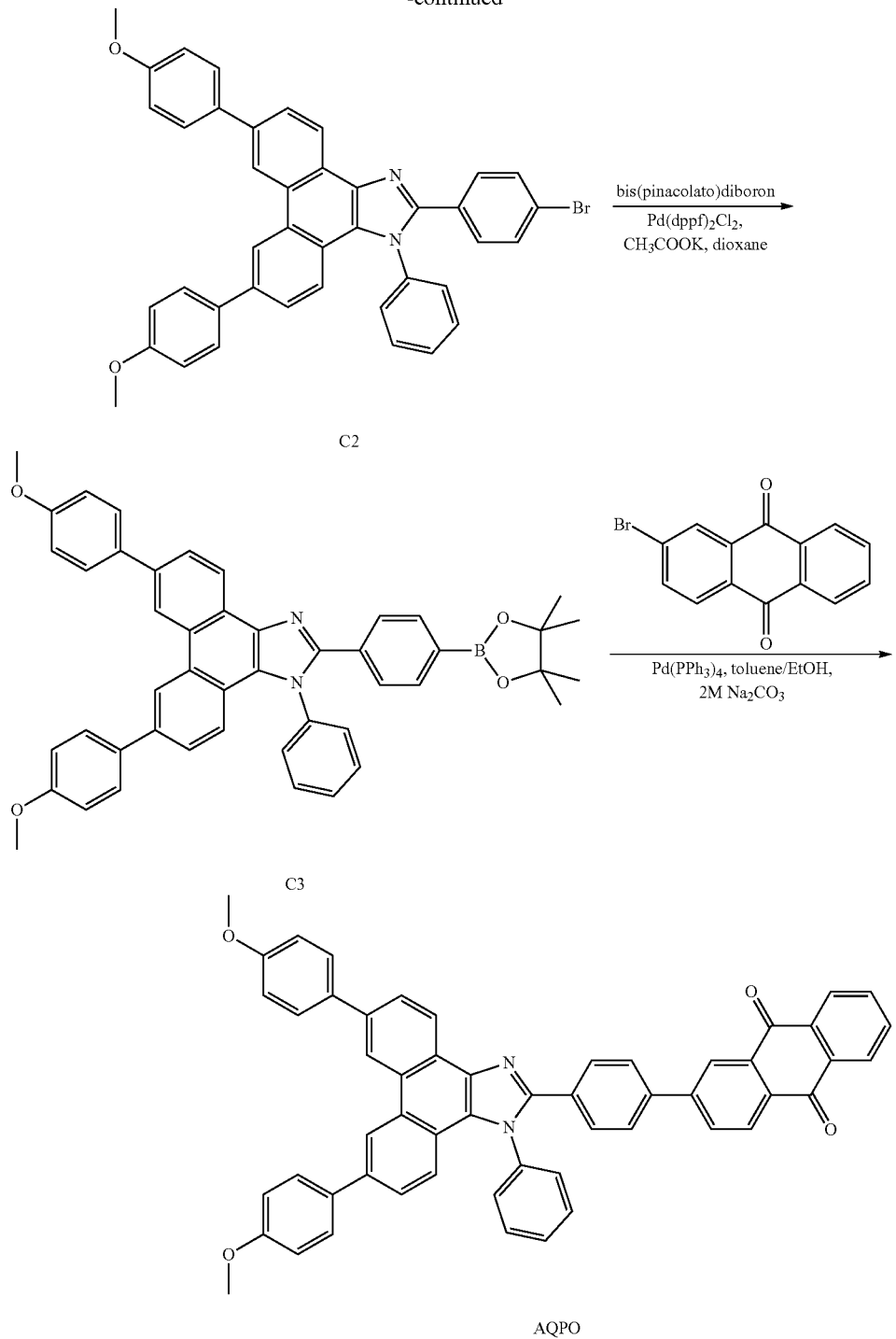

Figure 2:
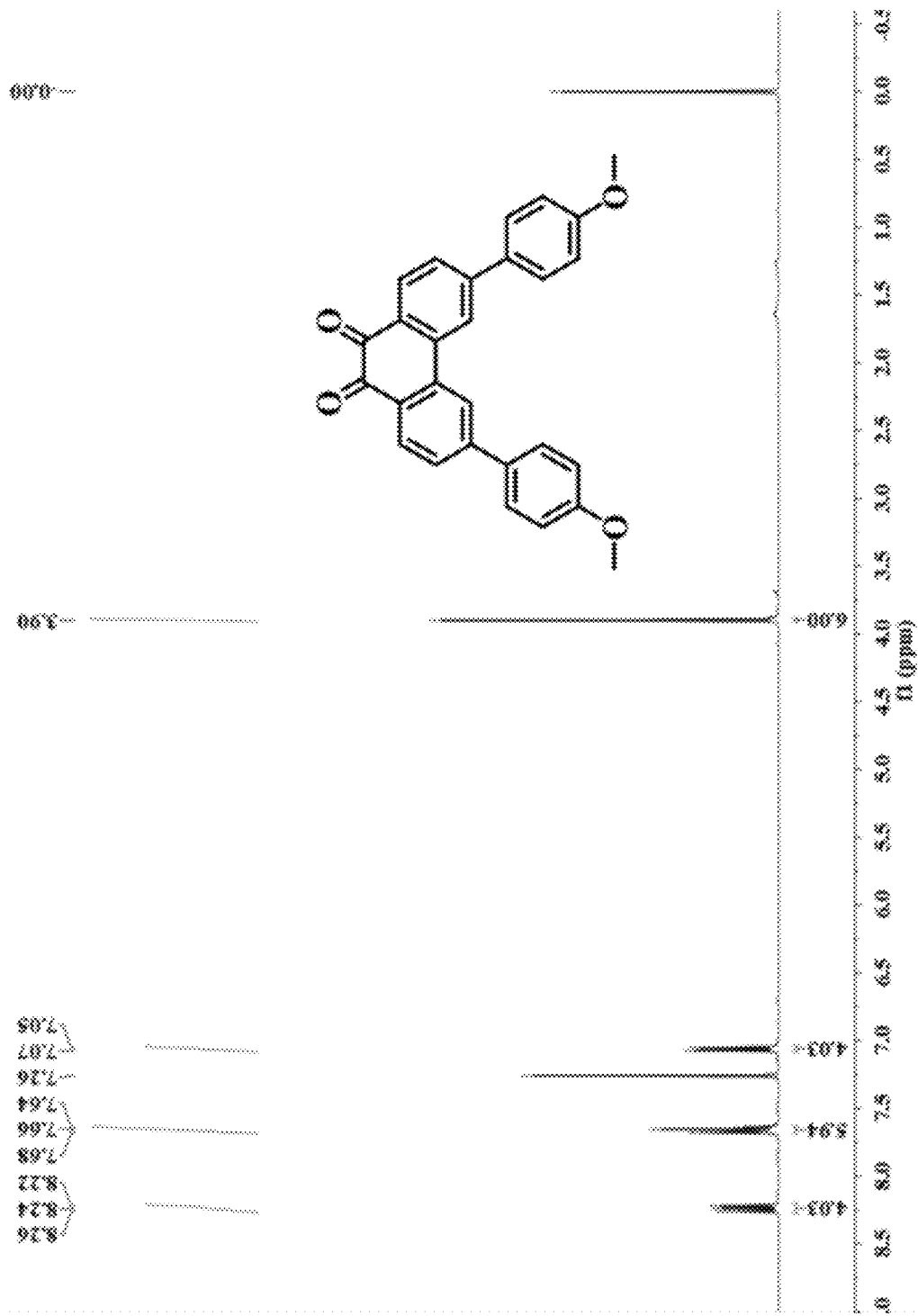
FIG. 2 shows a ¹H nuclear magnetic resonance (NMR) spectrum of a precursor compound of Formula (VIII) prepared in an embodiment of the present invention.

To a three-necked flask (100 mL), 3,6-dibromophenanthrene-9,10-dione (1.81 g, 5 mmol), (4-methoxyphenyl)boronic acid (1.52 g, 10 mmol), Pd(PPh$_3$)$_4$ (0.55 g, 0.5 mmol) and 40 mL of toluene/EtOH (3:1) were added under nitrogen atmosphere, followed by the addition of 20 mL of degassed Na$_2$CO$_3$ (aq. 2 M). The mixture was heated to 90° C. with stirring. After 12 h, the mixture was cooled down and washed with deionized water and then extracted with CHCl$_3$. The organic layer was dried under vacuum and the residue solid was purified by column chromatography using CHCl$_3$ to obtain the product (i.e. 3,6-bis(4-methoxyphenyl)phenanthrene-9,10-dione (Formula (VIII)) (1.64 g, 78%). The molecular structure was confirmed by NMR (FIG. 2) and mass spectroscopy (MS). $^1$H NMR (400 MHz, CDCl$_3$) δ 8.27-8.20 (m, 4H), 7.66 (t, J=7.9 Hz, 6H), 7.06 (d, J=8.7 Hz, 4H), 3.90 (s, 6H). MALDI-TOF MS (mass m/z): 420.322 [M]$^+$ calcd for C$_{28}$H$_{20}$O$_4$ 420.136.

Figure 3:
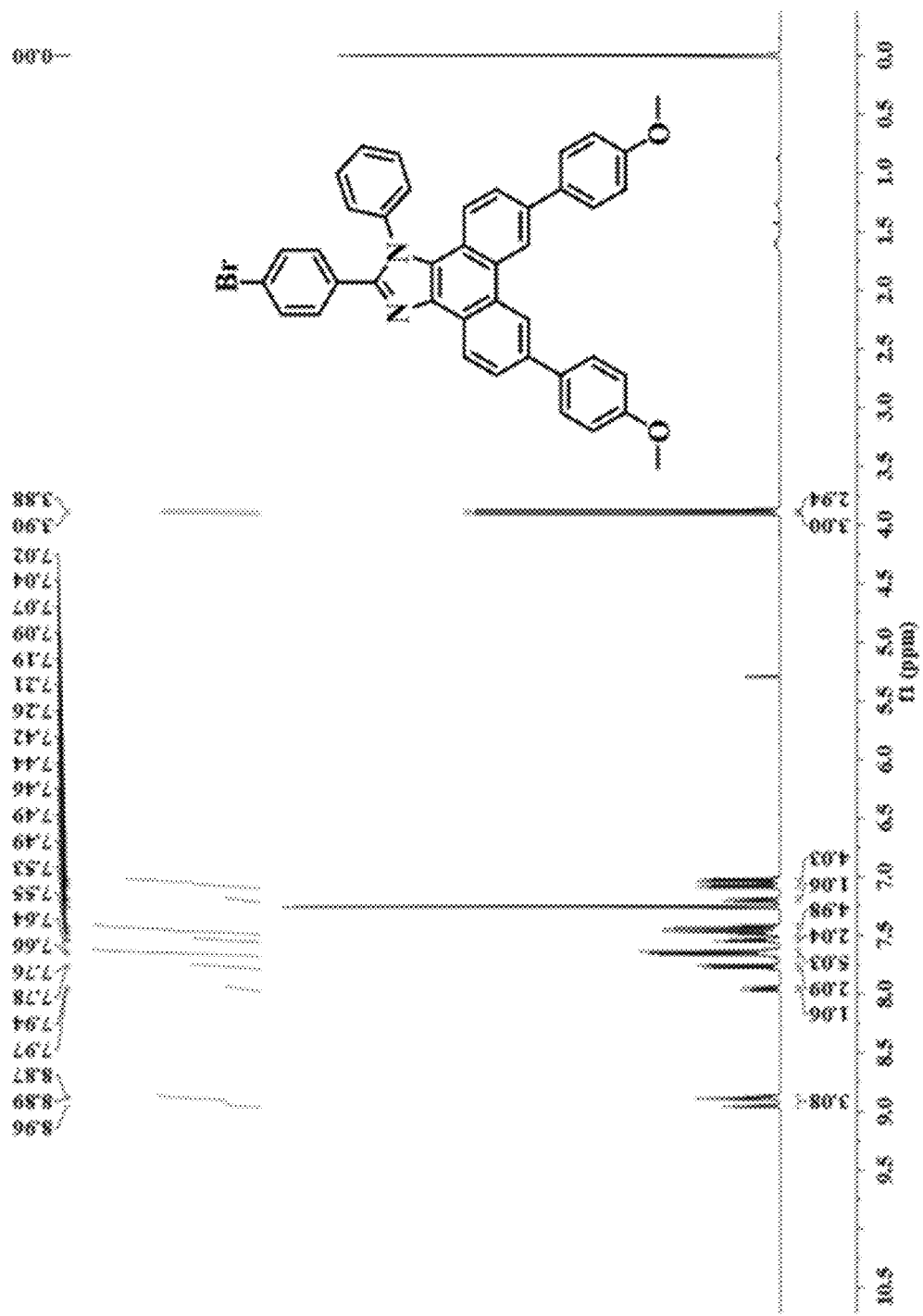
FIG. 3 shows a ¹H NMR spectrum of 2-(4-bromophenyl)-6,9-bis(4-methoxyphenyl)-1-phenyl-1H-phenanthro[9,10-d]imidazole prepared in an embodiment of the present invention.

Compound of Formula (VIII) (1.26 g, 3 mmol), aniline (0.33 mL, 3.6 mmol), 4-bromobenzaldehyde (0.55 g, 7 mmol), ammonium acetate (2.31 g, 30 mmol) and 30 mL of glacial acetic acid were added into a three-necked flask (100 mL), followed by refluxing the mixture for 24 h under a nitrogen atmosphere. After cooling, the mixture was poured into methanol with stirring. Then, the solid in the methanol mixture was collected and washed with methanol. The solid was purified by column chromatography on silica gel to obtain 2-(4-bromophenyl)-6,9-bis(4-methoxyphenyl)-1-phenyl-1H-phenanthro [9,10-d]imidazole (1.74 g, 88%). The molecular structure was confirmed by NMR (FIG. 3) and mass spectroscopy (MS). $^1$H NMR (400 MHz, CDCl$_3$) δ 8.91 (t, J=17.0 Hz, 3H), 7.96 (d, J=9.3 Hz, 1H), 7.77 (d, J=8.6 Hz, 2H), 7.65 (d, J=8.3 Hz, 5H), 7.54 (d, J=6.6 Hz, 2H), 7.49-7.40 (m, 5H), 7.20 (d, J=8.6 Hz, 1H), 7.05 (dd, J=19.6, 8.7 Hz, 4H), 3.90 (s, 3H), 3.88 (s, 3H). MALDI-TOF MS (mass m/z): 660.376 [M]$^+$ calcd for $C_{41}H_{29}BrN_2O_2$ 660.141.

Figure 4:
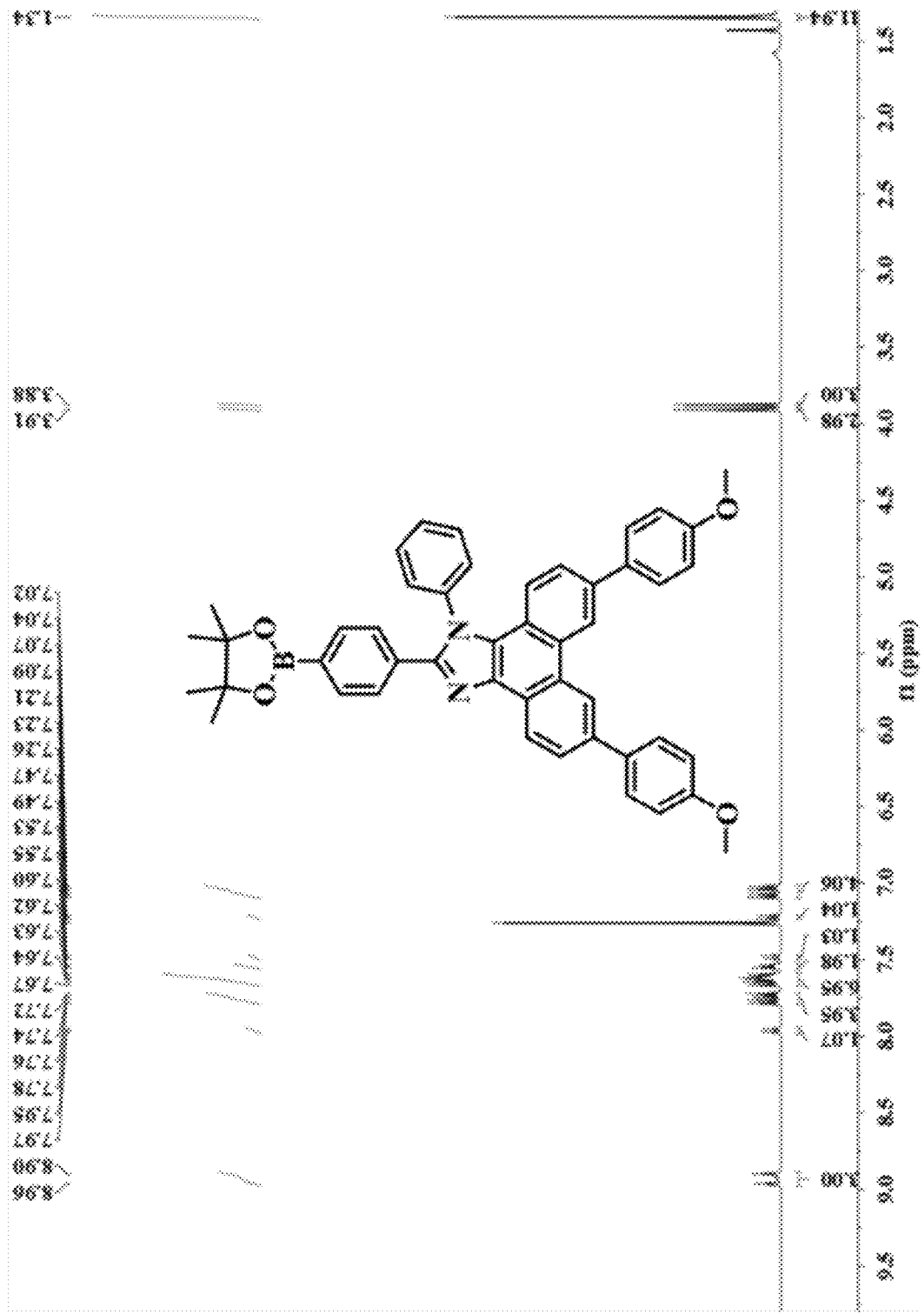
FIG. 4 shows a ¹H NMR spectrum of 6,9-bis(4-methoxyphenyl)-1-phenyl-2-(4-(4,4,5,5-tetramethyl-1,3,2-dioxaborolan-2-yl)phenyl)-1H-phenanthro[9,10-d]imidazole prepared in an embodiment of the present invention.

2-(4-bromophenyl)-6,9-bis(4-methoxyphenyl)-1-phenyl-1H-phenanthro[9,10-d]imidazole (1.32 g, 2 mmol), bis(pinacolato)diboron (0.58 g, 2 mmol), Pd(PPh$_3$)$_4$ (0.11 g, 0.1 mmol) and CH$_3$COOK (0.39 g, 4 mmol) were dissolved into dioxane (20 mL) under a nitrogen atmosphere, and then heated to 95° C. and stirred for one day. After cooling, water and dichloromethane (DCM) were added into the mixture for extraction. The organic layer was collected and dried with Na$_2$CO$_3$. The organic layer was then concentrated and purified by column chromatography on silica gel to obtain 6,9-bis(4-methoxyphenyl)-1-phenyl-2-(4-(4,4,5,5-tetramethyl-1,3,2-dioxaborolan-2-yl)phenyl)-1H-phenanthro[9,10-d]imidazole (0.71 g, 50%). The molecular structure was confirmed by NMR (FIG. 4) and mass spectroscopy (MS). $^1$H NMR (400 MHz, CDCl$_3$) δ 8.93 (d, J=25.9 Hz, 3H), 7.96 (d, J=8.4 Hz, 1H), 7.75 (dd, J=17.3, 8.3 Hz, 4H), 7.67-7.59 (m, 7H), 7.54 (d, J=6.7 Hz, 2H), 7.48 (d, J=8.6 Hz, 1H), 7.22 (d, J=8.6 Hz, 1H), 7.06 (dd, J=20.0, 8.6 Hz, 4H), 3.91 (s, 3H), 3.88 (s, 3H), 1.34 (s, 12H). MALDI-TOF MS (mass m/z): 708.691 [M]$^+$ calcd for $C_{47}H_{41}BN_2O_4$ 708.316.

Figure 5:
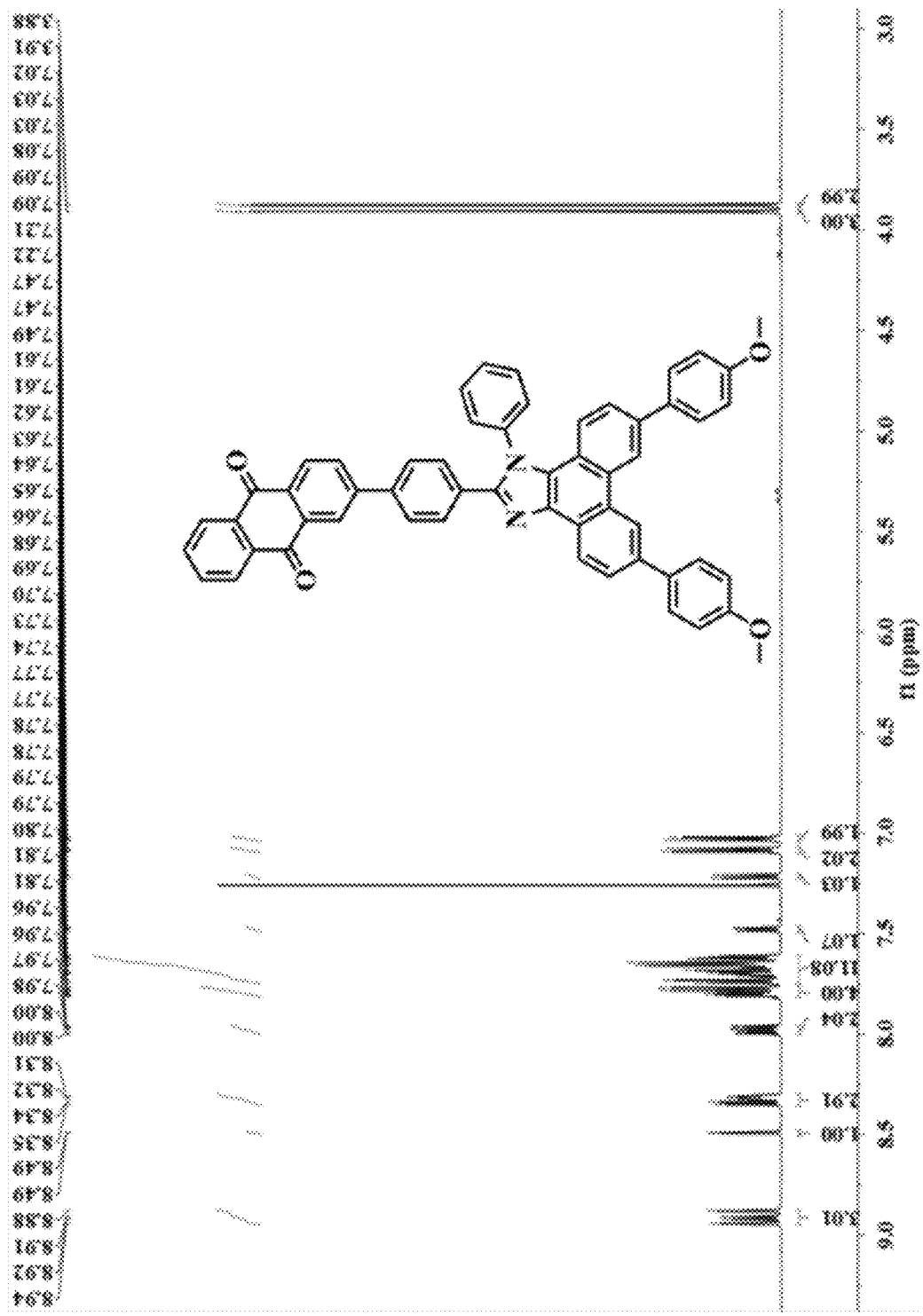
FIG. 5 shows a ¹H NMR spectrum of a compound of Formula (IV) prepared in an embodiment of the present invention.
Figure 6:
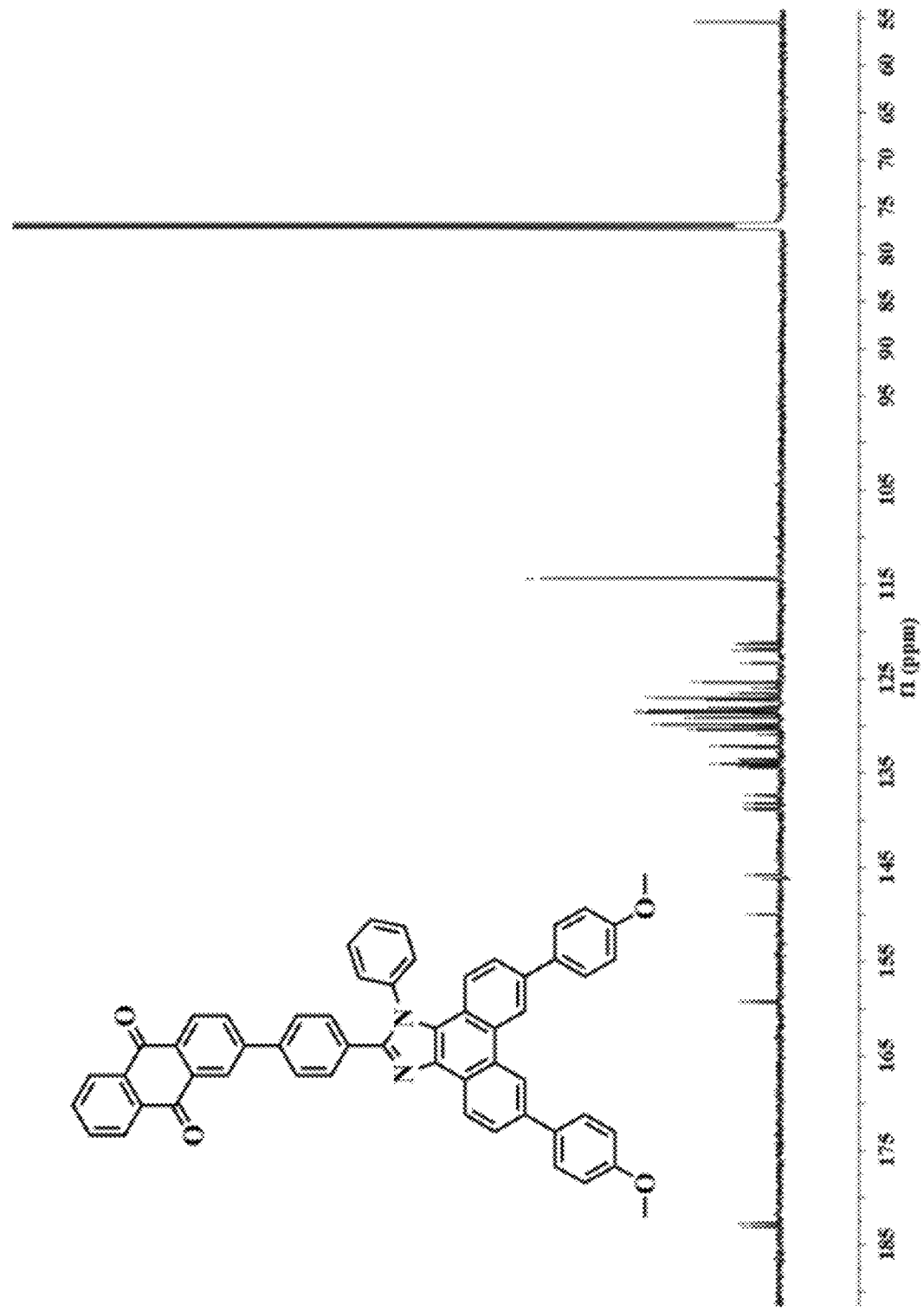
FIG. 6 shows a ¹³C NMR spectrum of a compound of Formula (IV) prepared in an embodiment of the present invention.

To a three-necked flask (100 mL), 2-bromoanthracene-9,10-dione (0.14 g, 0.5 mmol), 6,9-bis(4-methoxyphenyl)-1-phenyl-2-(4-(4,4,5,5-tetramethyl-1,3,2-dioxaborolan-2-yl)phenyl)-1H-phenanthro[9,10-d]imidazole (0.71 g, 1 mmol), Pd(PPh$_3$)$_4$ (0.05 g, 0.05 mmol) and 10 mL of toluene/EtOH (3:1) were under nitrogen atmosphere, followed by the addition of 2 mL of degassed Na$_2$CO$_3$ (aq. 2 M). The mixture was heated to 90° C. with stirring. After 12 h, the mixture was cooled down and washed with deionized water and then extracted with CHCl$_3$. The organic layer was dried under vacuum and the residue solid was purified by column chromatography using CHCl$_3$ to obtain the product (i.e. 2-(4-(6,9-bis(4-methoxyphenyl)-1-phenyl-1H-phenanthro[9,10-d]imidazol-2-yl)phenyl)anthracene-9,10-dione, Compound A having the structure of Formula (IV)) (0.28 g, 70%). The molecular structure was confirmed by NMR (FIGS. 5 and 6) and mass spectroscopy (MS). $^1$H NMR (600 MHz, CDCl$_3$) δ 8.91 (dd, J=22.7, 14.5 Hz, 3H), 8.49 (d, J=1.8 Hz, 1H), 8.36-8.30 (m, 3H), 7.98 (ddd, J=14.2, 8.1, 1.7 Hz, 2H), 7.81-7.76 (m, 4H), 7.75-7.61 (m, 11H), 7.48 (dd, J=8.6, 1.7 Hz, 1H), 7.22 (d, J=8.5 Hz, 1H), 7.10-7.07 (m, 2H), 7.04-7.01 (m, 2H), 3.91 (s, 3H), 3.88 (s, 3H). $^{13}$C NMR (151 MHz, CDCl$_{13}$) δ 183.10, 182.75, 159.28, 159.21, 149.96, 146.20, 145.80, 138.85, 138.74, 138.21, 137.43, 137.35, 134.39, 134.18, 134.05, 133.86, 133.69, 133.61, 133.54, 132.28, 132.13, 130.93, 130.37, 130.06, 130.02, 129.85, 129.81, 129.16, 128.72, 128.61, 128.46, 128.39, 128.05, 127.28, 127.21, 127.05, 126.60, 126.02, 125.42, 123.31, 121.96, 121.74, 121.34, 121.18, 114.36, 55.44, 55.40. MALDI-TOF MS (mass m/z): 788.676 [M] calcd for $C_{55}H_{36}N_2O_4$ 788.268.

Example 2

Preparation of Nanoparticle of Compound A

Figure 7A:
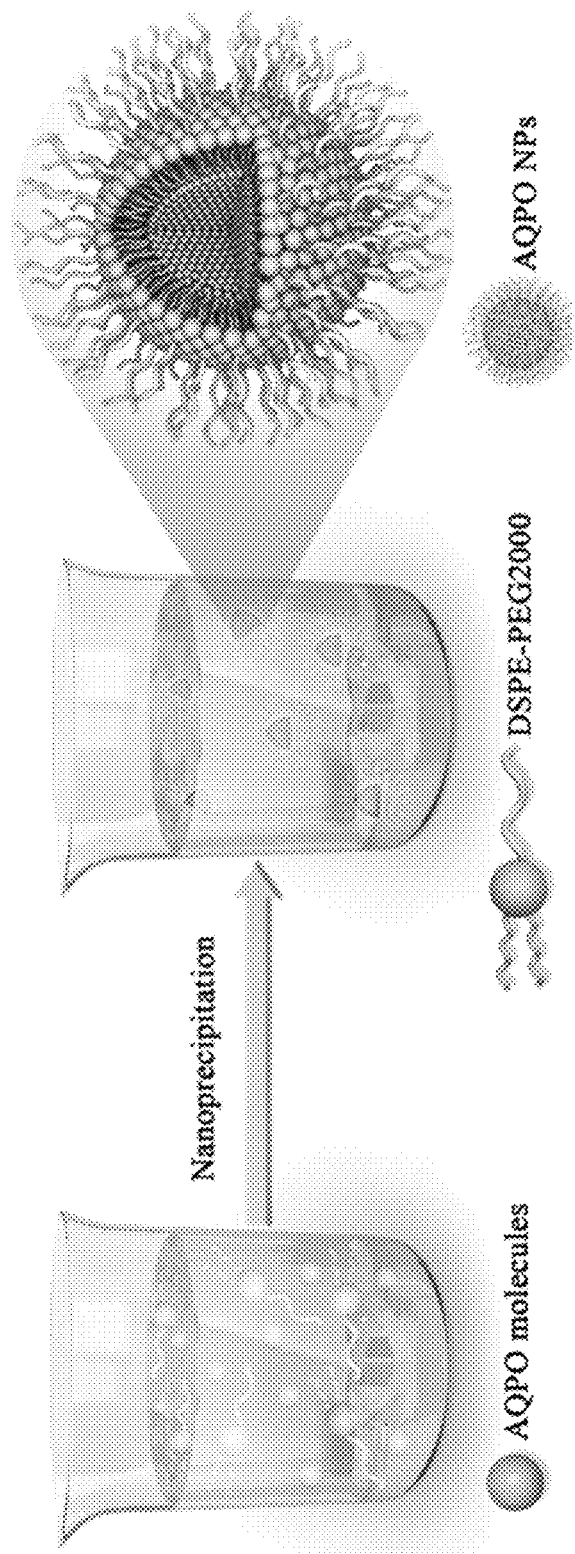
FIG. 7A shows a schematic diagram illustration for nanoprecipitation of Compound A of Formula (IV) according an embodiment of the present invention.

To fabricate nanoparticle of Compound A (i.e. AQPO NPs) as a water-dispersible PS, an amphiphilic block copolymer DSPE-PEG 2000 was used to assemble AQPO molecules as biocompatible AQPO nanoparticles (NPs) by a facile nanoprecipitation method (FIG. 7A). The detailed procedures are as follows:

0.5 mL of AQPO/THF (0.5 mg/mL) and 0.5 mL of DSPE-PEG2000/THF (5 mg/mL) were fully mixed and then added dropwise into 10 mL of DI water under 1200 rpm magnetic stirring at 25° C. for 1 h. Then THF was removed by rotary evaporator, obtaining the crude form of nanoparticle of Compound A (i.e. AQPO NPs) dispersions. The crude form of AQPO NPs were purified and concentrated using a 100,000 MWCO Millipore. The AQPO NPs dispersions were stored at 4° C. for future use.

Figure 7C:
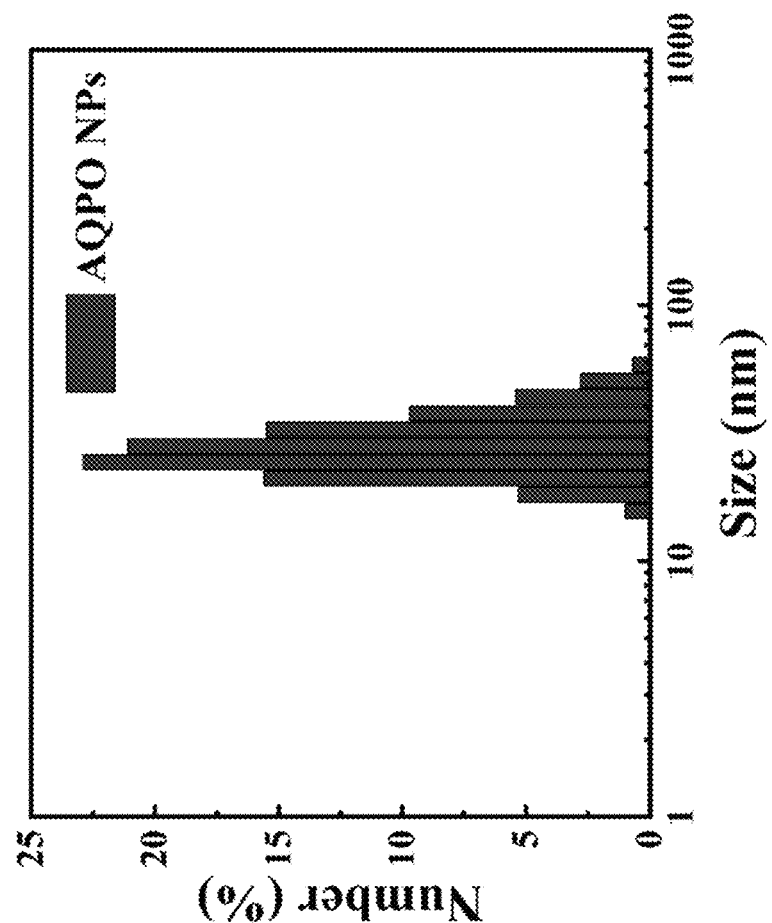
FIG. 7C shows size distributions of nanoparticle of Compound A of Formula (IV) prepared in an embodiment of the present invention.
Figure 7B:
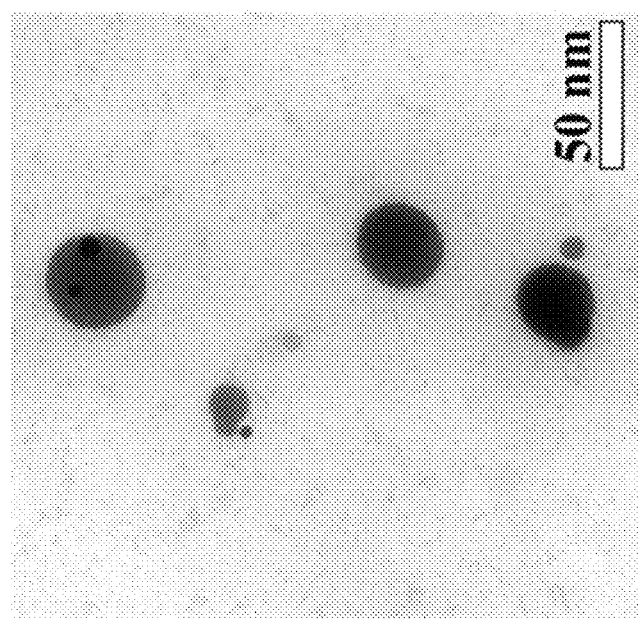
FIG. 7B shows a transmission electron microscopy (TEM) image of nanoparticle of Compound A of Formula (IV) prepared in an embodiment of the present invention.

The as-formed AQPO NPs were characterized by transmission electron microscopy (TEM) and dynamic light scattering (DLS). As revealed by FIG. 7B, AQPO NPs of the present invention shows a spherical and uniform morphology. DLS measurement also revealed that the AQPO NPs have an average hydrodynamic diameter of about 29.08 nm±1.48 nm (FIG. 7C).

Example 2A

Preparation of Ce6 NPs

The FDA-approved Ce6 NPs were used as a control in subsequent experiments. The synthetic procedures of Ce6 are as follows: 0.5 mL of Ce6/DMSO (0.5 mg/mL) and 0.5 m L of DSPE-PEG2000/DMSO (5 mg/mL) were fully mixed and then added dropwise into 10 mL of DI water under 1200 rpm magnetic stirring at 25° C. for 1 h. The crude Ce6 NPs suspensions were stirring overnight and then dialyzed with 3.5 kDa MWCO in 4 h to remove DMSO and free Ce6. The crude Ce6 NPs were purified and concentrated using a 100,000 MWCO Millipore. The Ce6 NPs dispersions were stored at 4° C. for future use.

Example 3

Evaluation of ROS Generation Capacity of Nanoparticle of Compound A

The ROS generation abilities of AQPO NPs have been investigated by various ROS indicators, including 2,7-dichlorodihydrofluorescein diacetate (DCFH-DA, a general ROS indicator), 9,10-anthracenediylbis(methylene)-dimalonic acid (ABDA, an $^1O_2$ indicator), dihydrorhodamine 123 (DHR123, an $O_2^-$ indicator) and hydroxyphenyl fluorescein (HPF, an OH. indicator).

Figures 8A, 8B:
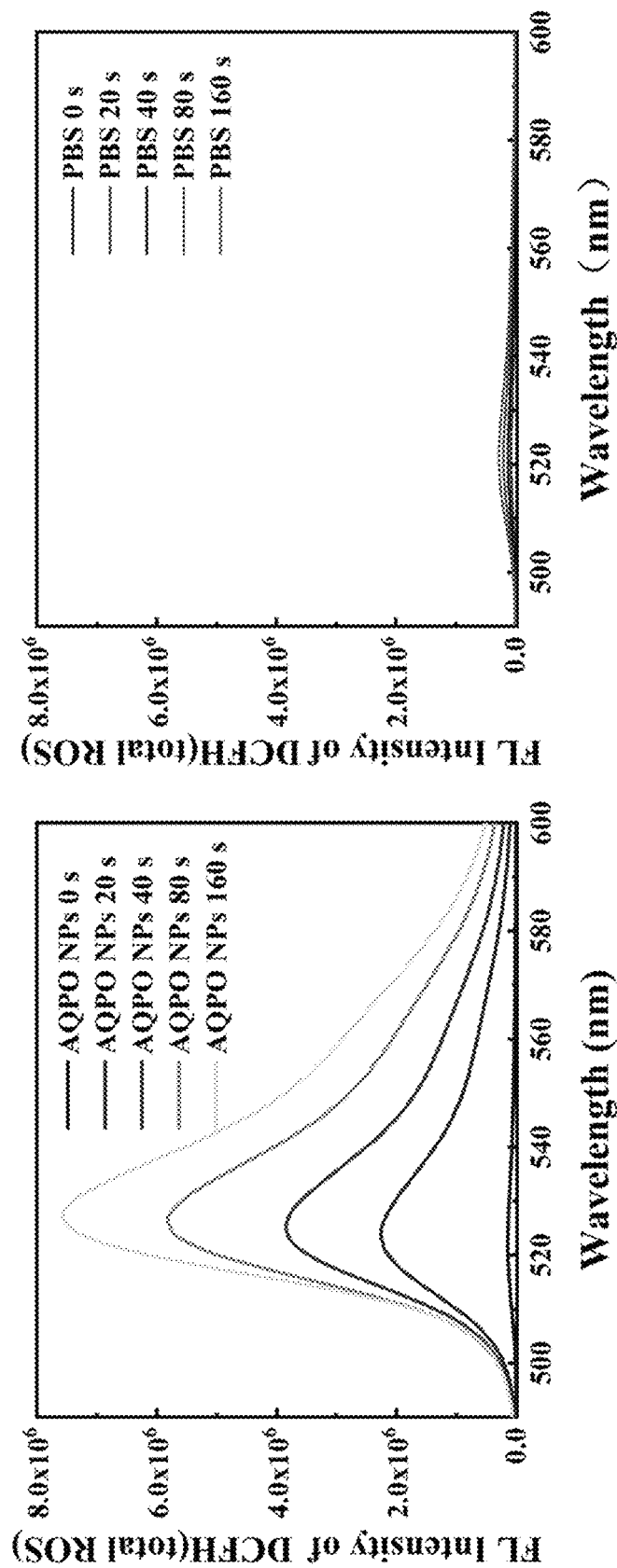
FIG. 8A shows fluorescence spectra of DCFH solutions with nanoparticle of Compound A of Formula (IV) prepared in an embodiment under different irradiation time.
FIG. 8B shows fluorescence spectra of DCFH solutions with PBS under different irradiation time.

The total ROS generation was first investigated. To do so, the AQPO NPs were added into DCFH/DI water solution (5 μM) under white light irradiation (50 mW/cm$^2$) for different time intervals. The fluorescence intensity of DCFH was measured by the spectrofluorometer to investigate the total ROS generation (Ex: 490 nm). DCFH aqueous solution with PBS was used as a control. As shown in FIG. 8A, the AQPO NPs show a significant increase in DCFH fluorescence under irradiation as compared with the PBS group (control) (FIG. 8B), indicating the excellent total ROS generation ability of the AQPO NPs.

Figure 9B:
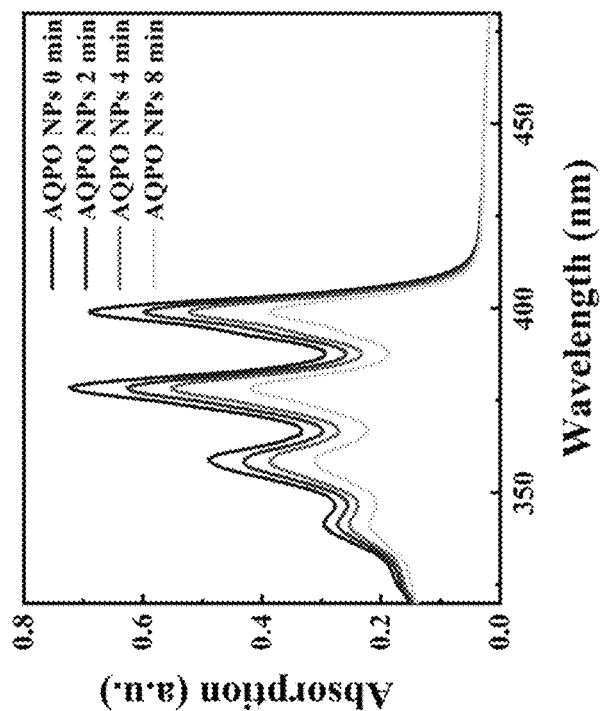
FIG. 9B shows absorption spectra of ABDA solutions with nanoparticle of Compound A of Formula (IV) prepared in an embodiment under different irradiation time.
Figure 9A:
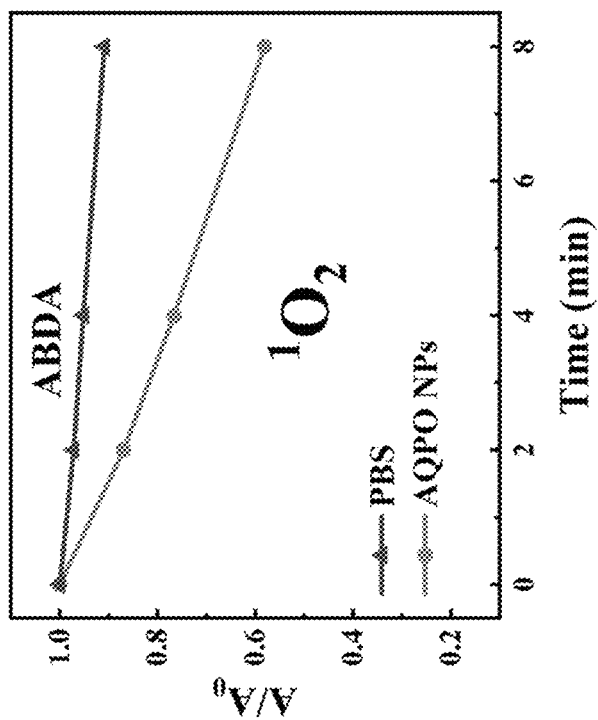
FIG. 9A shows a plot illustrating ABDA activated rates of fluorescence by nanoparticle of Compound A of Formula (IV) prepared in an embodiment and PBS with the same area of integral absorption under white light irradiation (50 mW/cm$^2$). A and $A_0$ denote the absorption intensity of ABDA at 399 nm before and after light irradiation.
Figure 9D:
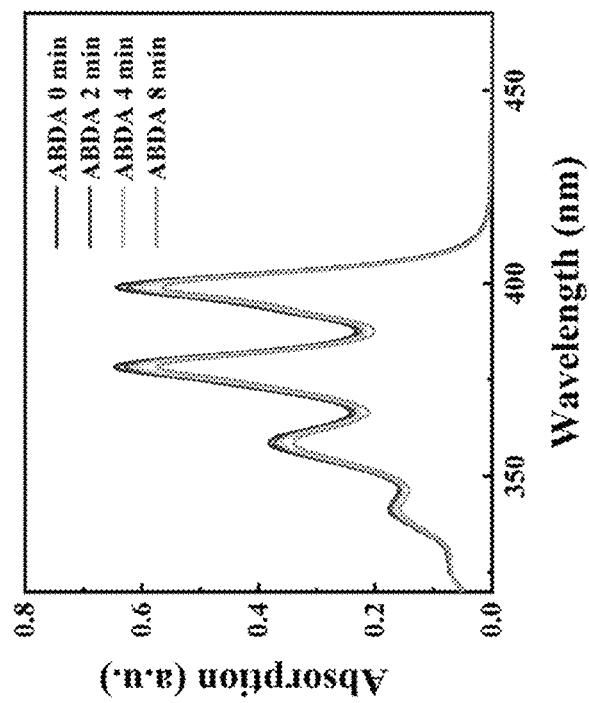
FIG. 9D shows absorption spectra of ABDA solutions with PBS under different irradiation time.
Figure 9C:
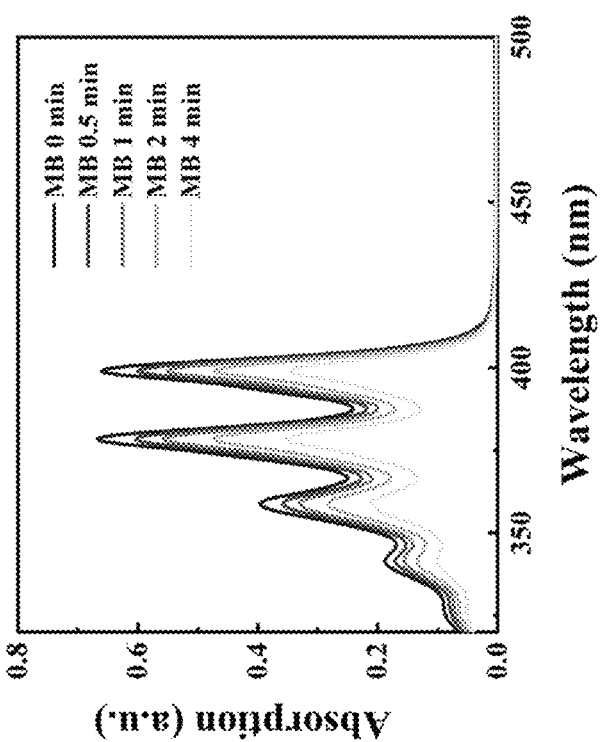
FIG. 9C shows absorption spectra of ABDA solutions with MB under different irradiation time.
Figure 9F:
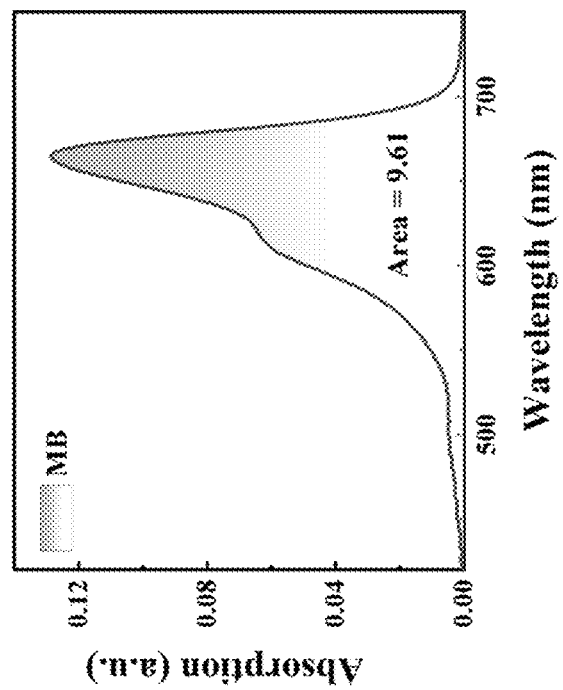
FIG. 9F shows an absorption spectrum of MB and the corresponding integral area from 300 nm to 700 nm, which is used for the calculation of $\Phi_A$.
Figure 9E:
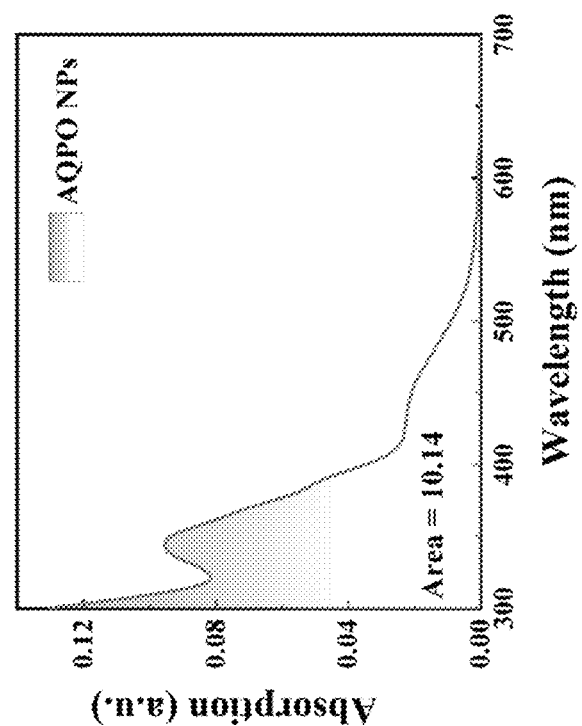
FIG. 9E shows an absorption spectrum of nanoparticle of Compound A of Formula (IV) prepared in an embodiment and the corresponding integral area from 300 nm to 700 nm, which is used for the calculation of $\Phi_{66}$.

The $^1O_2$ quantum yields of AQPO NPs was next investigated. The measurement was performed by using ABDA as a sensor under irradiation with a xenon lamp. The absorption of ABDA decreases proportionably with increased $^1O_2$ in the water phase. Methylene blue (MB) was used as a calibration standard ($\Phi_A$=0.52). The decreased absorption of ABDA was monitored by a ultra-violet and visible spectrophotometer. All samples were irradiated with a xenon lamp of 50 mW/cm². The absorption maxima of MB and the NPs were adjusted to ~0.15-0.25 OD. $\Phi_A$ of the NPs were calculated using the following formula:

$$\Phi_\Delta(\text{sample}) = \frac{\Phi_\Delta(MB) \times K_{sample} \times A_{MB}}{K_{MB} \times A_{sample}}, \quad \text{Formula (2)}$$

where $K_{sample}$ and $K_{MB}$ are the decrease rate constants of the ABDA by the NPs and MB at 399 nm, respectively. $A_{MB}$ and $A_{sample}$ represent the absorption integral of the MB and NPs in the wavelength range 300-700 nm, respectively. As shown in FIG. 9A, AQPO NPs show a massive production of $^1O_2$ as compared with the PBS group (control), and the $^1O_2$ quantum yield of AQPO NPs was determined as 18% (FIG. 9B to FIG. 9F).

Figure 10B:
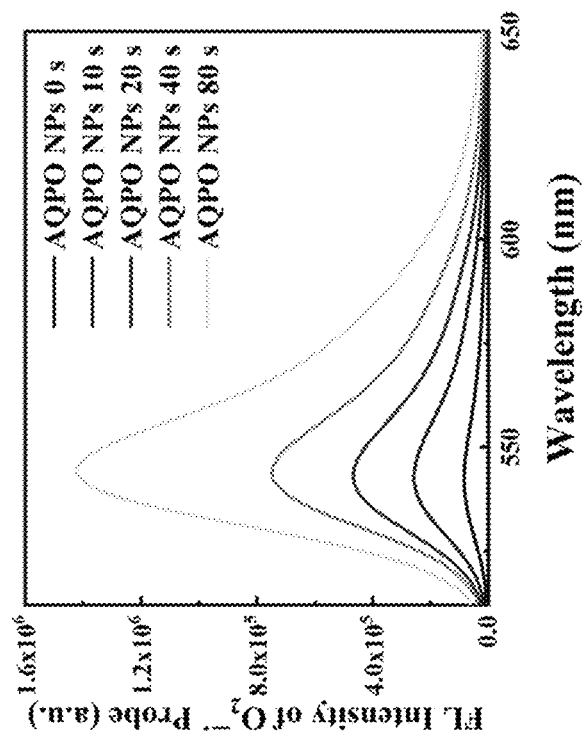
FIG. 10B shows fluorescence spectra of DHR123 solutions with nanoparticle of Compound A of Formula (IV) prepared in an embodiment under the same area of integral absorption with Ce6 NPs for different irradiation time.
Figure 10A:
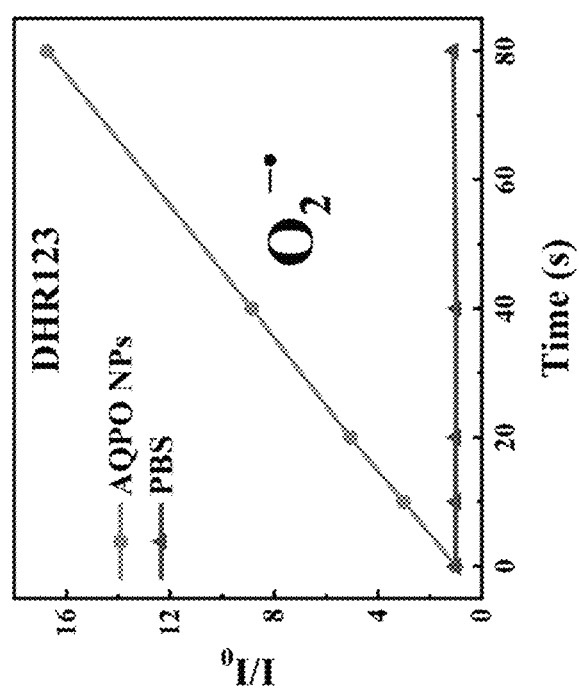
FIG. 10A shows a plot illustrating DHR123 activated rates of fluorescence by nanoparticle of Compound A of Formula (IV) prepared in an embodiment and PBS with the same area of integral absorption under white light irradiation (50 mW/cm$^2$). I and $I_0$ denote the fluorescence intensity of DHR123 at 543 nm before and after light irradiation, respectively.
Figure 10C:
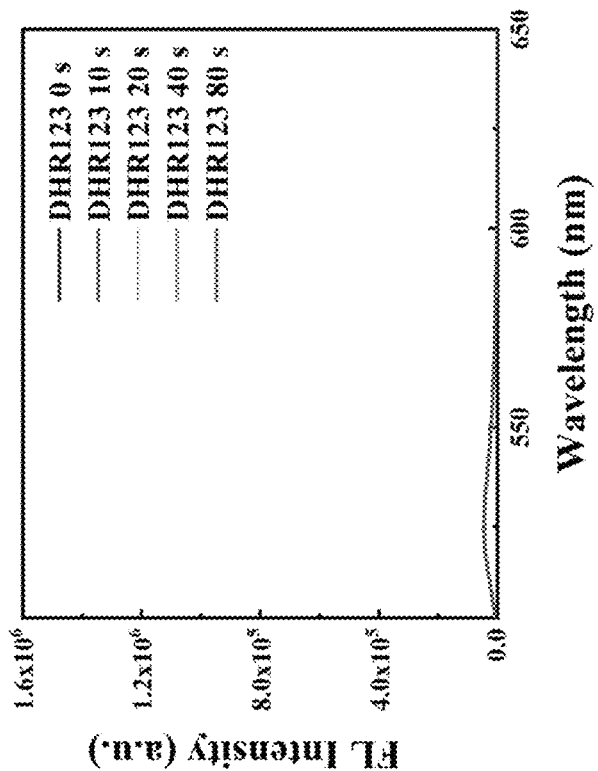
FIG. 10C shows fluorescence spectra of DHR123 solutions with Ce6 NPs under the same area of integral absorption with nanoparticle of Compound A of Formula (IV) prepared in an embodiment for different irradiation time.
Figure 10D:
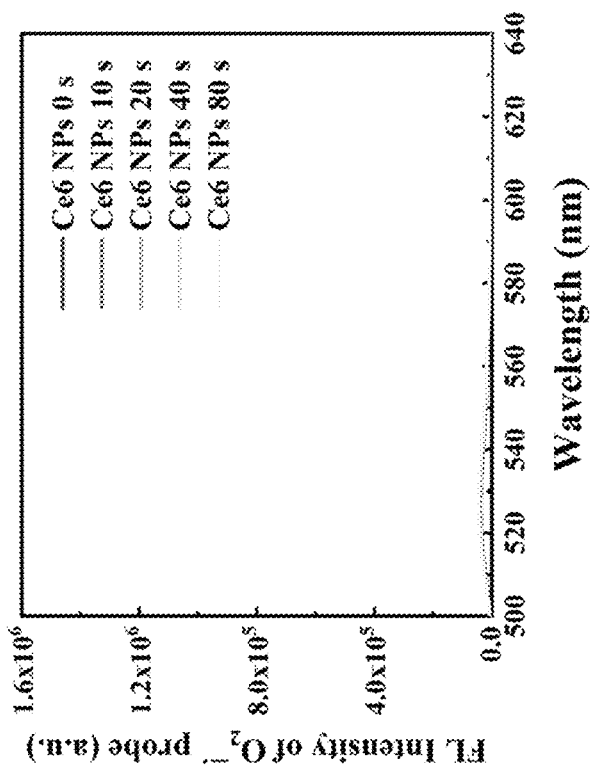
FIG. 10D shows fluorescence spectra of DHR123 solutions with PBS for different irradiation time.
Figure 11:
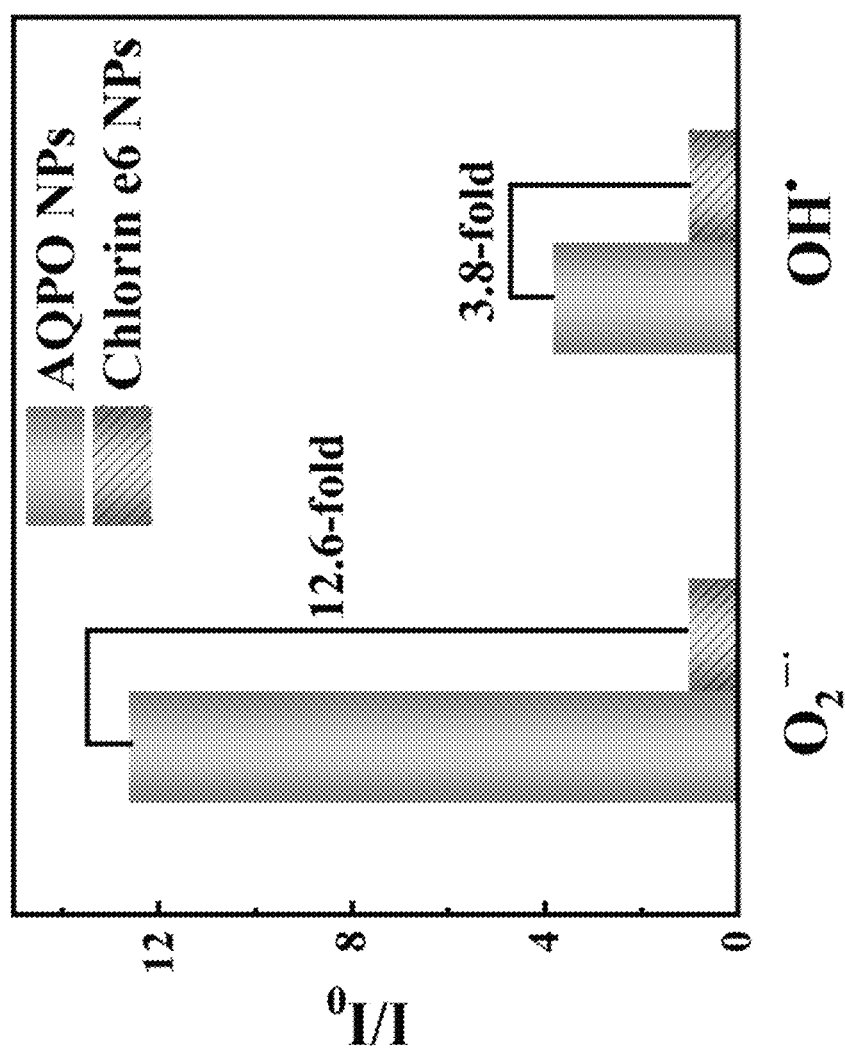
FIG. 11 shows a bar chart illustrating the comparison of $O_2^-$· and OH· generation efficiencies of nanoparticle of Compound A of Formula (IV) prepared in an embodiment and Ce6 NPs under the same experimental conditions.

To determine the $O_2^-$. generation, AQPO NPs or Ce6 NPs were added into DHR123/DI water solution (10 μM) with the same area of integral absorption (area: ~16) under white light irradiation (50 mW/cm²) for different time intervals. The fluorescence intensity of DHR123 was measured by the spectrofluorometer to investigate the $O_2^-$. generation (Ex: 480 nm). DHR123 aqueous solution with PBS was used as a control. As shown in FIG. 10A, the fluorescence of DHR123 with AQPO NPs shows an impressive increase under irradiation as compared with the PBS control. In addition, a similar significant increase in the fluorescence was observed when the result of AQPO NPs was compared with that of the Ce6 NPs, indicating the high $O_2^-$. production efficiency of AQPO NPs (FIG. 10B to FIG. 10D). In particular, it was found that the $O_2^-$. production efficiency of AQPO NPs to be about 12.6-fold more than that of Ce6 NPs under the same experimental conditions (FIG. 11).

Figure 12D:
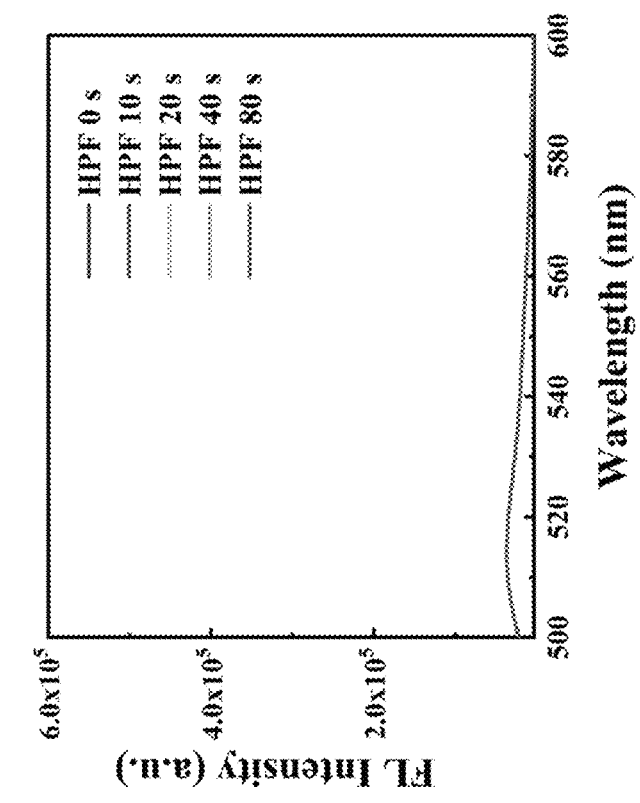
FIG. 12D shows fluorescence spectra of HPF solutions with PBS for different irradiation time.
Figure 12C:
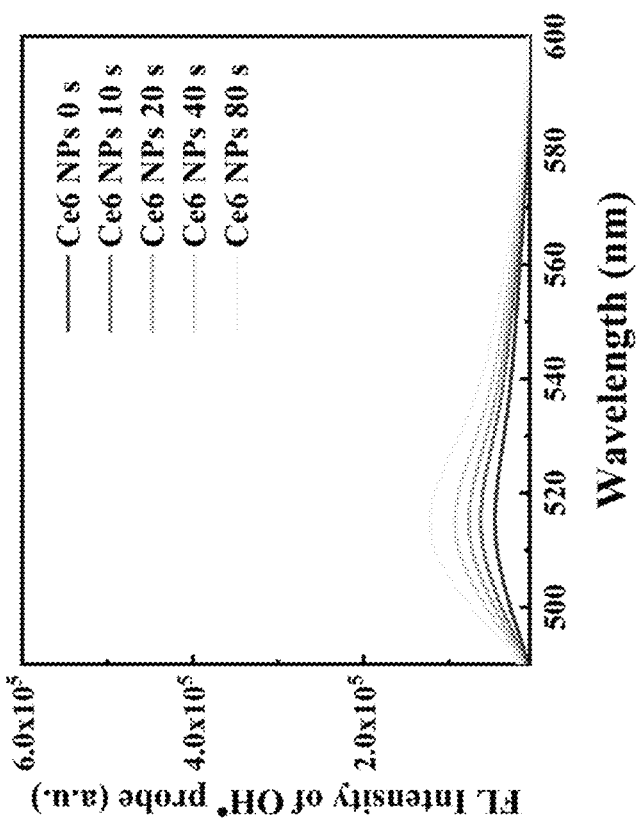
FIG. 12C shows fluorescence spectra of HPF solutions with Ce6 NPs under the same area of integral absorption with nanoparticle of Compound A of Formula (IV) prepared in an embodiment for different irradiation time.

To determine the OW generation, AQPO NPs or Ce6 NPs were added into HPF (a fluorescence turn-on probe)/1×PBS water solution (10 μM) with the same area of integral absorption (area: ~16) under white light irradiation (50 mW/cm²) for different time intervals. The fluorescence intensity of HPF was monitored to measure OW originating from the oxidation of water under irradiation by the spectrofluorometer to investigate the OW generation (Ex: 460 nm). HPF aqueous solution was used as control. As revealed by FIG. 12A, the significant increase in fluorescence intensity of HPF in the presence of AQPO NPs as compared with that of PBS suggests that AQPO NPs generate abundant OW under irradiation. In addition, a similar significant increase in the fluorescence was observed when the result of AQPO NPs was compared with that of the Ce6 NPs, indicating the high OW production efficiency of AQPO NPs (FIG. 12B to FIG. 12D). In particular, as shown in FIG. 11, the OW generation efficiency of AQPO NPs was determined to be 3.8-fold higher than that of Ce6 NPs under the same experimental conditions.

Figure 13:
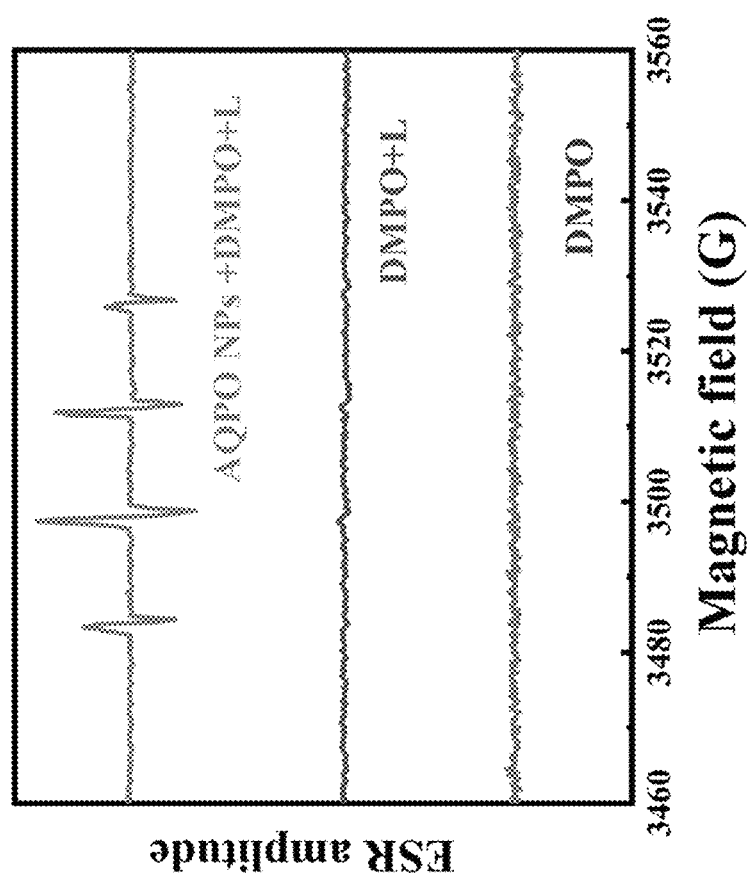
FIG. 13 shows ESR spectra of DMPO adducts in the presence or absence of nanoparticle of Compound A of Formula (IV) prepared in an embodiment in DI water, respectively. L refers to white light irradiation (50 mW/cm$^2$).

The inventors have further employed electron spin resonance (ESR) spectroscopy to detect radicals ($O_2^-$. and OH.) using 5,5-dimethyl-1-pyrroline N-oxide (DMPO) as a spin-trap indicator. As depicted in FIG. 13, the DMPO adducts treated with AQPO NPs show a stronger ESR signal than that without NPs under irradiation, indicating plentiful $O_2^-$./OH. generation by AQPO NPs. Based on the above-mentioned evidence, it can be concluded that the AQPO NPs display an excellent performance of multiple ROS generation in aqueous solution, including both Type-I ($O_2^-$./OH.) and Type-II ($^1O_2$).

Example 4

Cellular ROS Generation of Nanoparticle of Compound A

To investigate the cellular ROS generation of AQPO NPs, 2,7-dichlorodihydrofluorescein diacetate (DCFH-DA, a general ROS indicator) and dihydroethidium (DHE, an $O_2^-$. indicator) were applied. In this example, A549 cells were used for investigation. A549 cells were seeded into 35 mm microscopy dishes with a glass bottom and treated with AQPO NPs (15 μg/mL) for 4 h. Then, all the cells were stained by the DCFH-DA (or DHE) solution for 30 min in 37° C., followed by being irradiated under white light (50 mW/cm²) for different time intervals. Then the cells were stained by DiD (or DiO) for 5 min to label cell membrane. The fluorescence of DCFH-DA (or DHE) and DiD (or DiO) were observed by Confocal Laser Scanning Microscope (CLSM). As shown in FIG. 14A and FIG. 14B, the fluorescence intensities of DCFH-DA and DHE treated with AQPO NPs become gradually stronger in A549 cells under the light irradiation, manifesting effective production of ROS and $O_2^-$. The results indicate that upon irradiation, AQPO NPs can produce multiple ROS in cancer cells.

Example 5

Cellular Uptake and Localization of Nanoparticle of Compound A

Figure 15:
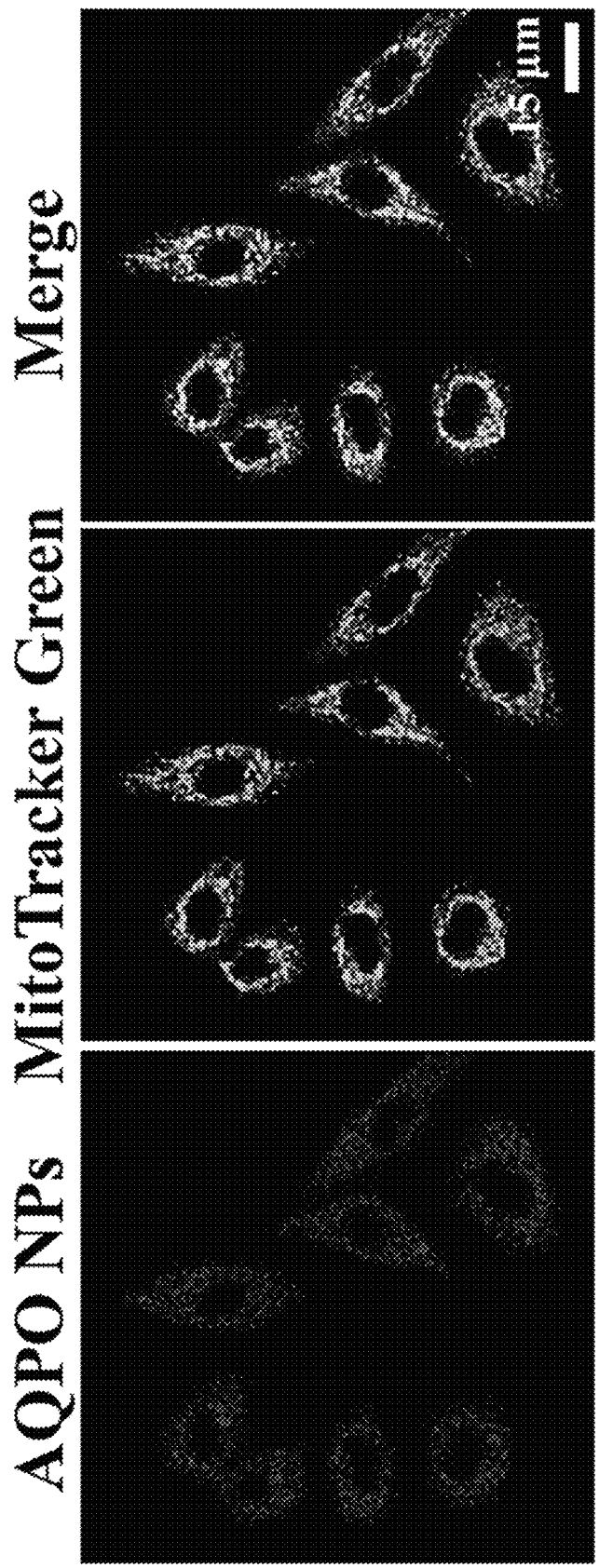
FIG. 15 shows CLSM images illustrating internalization and mitochondria co-localization of nanoparticle of Compound A of Formula (IV) prepared in an embodiment of the present invention in A549 cells. Scale bar=15 μm.

Cellular uptake images of AQPO NPs were taken using CLSM. A549 cells were seeded in a 35 mm microscopy dishes with glass bottom for 12 h and then incubated with AQPO NPs (8 μg/mL) for 4 h. Then the cells were stained by MitoTracker Green to label mitochondria. The fluorescence of AQPO NPs and MitoTracker Green were observed under the excitation of 405 nm and 488 nm, respectively. As shown in FIG. 15, the AQPO NPs are successfully internalized into the A549 cells and tend to accumulate in mitochondria.

Example 6

In Vitro PDT Evaluation of Nanoparticle of Compound a Under Hypoxia and Normoxia In vitro PDT effect of the AQPO NPs was investigated with a standard 3-(4,5-dimethylthiazol-2-yl)-2,5-diphenyltetrazolium bromide (MTT) assay. A549 or HeLa cells (~5000 cells/well) were seeded on a 96-well plate in 100 μL of complete DMEM medium for 24 h incubation. The AQPO NPs or Ce6 NPs were diluted into different concentrations with 1×PBS. The cells were incubated with different concentrations of AQPO NPs or Ce6 NPs for 4 h and then irradiated under white light (50 mW/cm²) for 5 min. After 20 h, the cell viabilities were measured. To evaluate the dark cytotoxicity, the same concentrations of AQPO NPs dispersions were added into A549 or HeLa cells in 96-well plate for 24 h in darkness, respectively, and then the cell viabilities were measured. The air conditions of incubators are 21% $O_2$+5% $CO_2$ (normoxia) and 2% $O_2$+5% $CO_2$ (hypoxia), respectively.

Figure 16A:
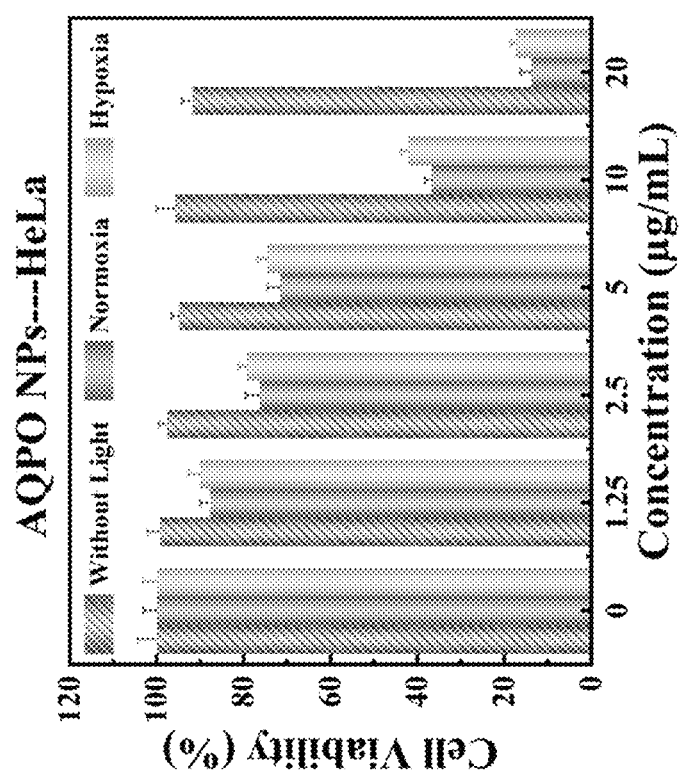
FIG. 16A shows a bar chart illustrating dark cytotoxicity and photocytotoxicity of nanoparticle of Compound A of Formula (IV) prepared in an embodiment of the present invention to A549 cells under normoxia and hypoxia.
Figure 16B:
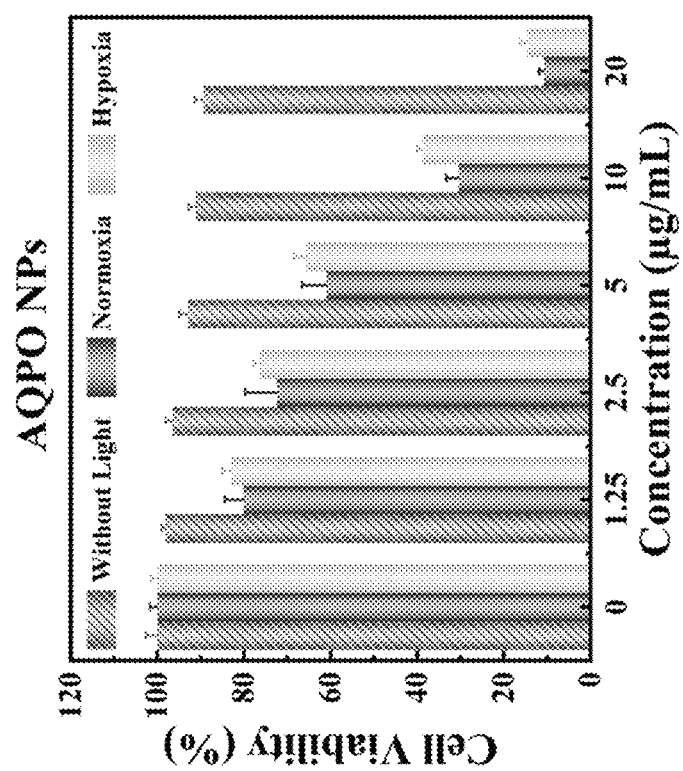
FIG. 16B shows a bar chart illustrating dark cytotoxicity and photocytotoxicity of nanoparticle of Compound A of Formula (IV) prepared in an embodiment of the present invention to HeLa cells under normoxia and hypoxia.

As depicted in FIG. 16A, AQPO NPs exhibited negligible dark cytotoxicity to A549 cells, however, a strong photocytotoxicity occurs with a dose-dependent manner under normoxia (21% $O_2$). More importantly, when the $O_2$ concentration artificially decreased to 2% to simulate a hypoxic environment, the AQPO NPs still exhibited a similar photocytotoxicity to the group under normoxia, suggesting that the AQPO NPs are photocytotoxic to A549 cells under both the hypoxia and normoxia conditions. Similar dark cytotoxicity and photocytotoxic behaviours were observed when A549 cells were replaced with HeLa cells (FIG. 16B). That is, the AQPO NPs displayed similar dose-dependent photocytotoxicity under both normoxic and hypoxic conditions, but negligible dark cytotoxicity under such conditions.

Figure 16C:
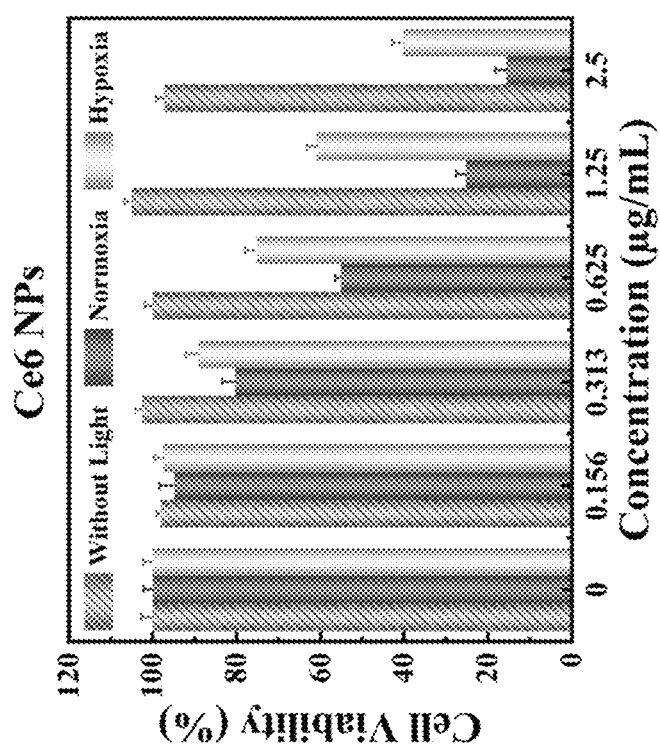
FIG. 16C shows a bar chart illustrating dark cytotoxicity and photocytotoxicity of Ce6 NPs to A549 cells under normoxia and hypoxia.
Figure 16D:
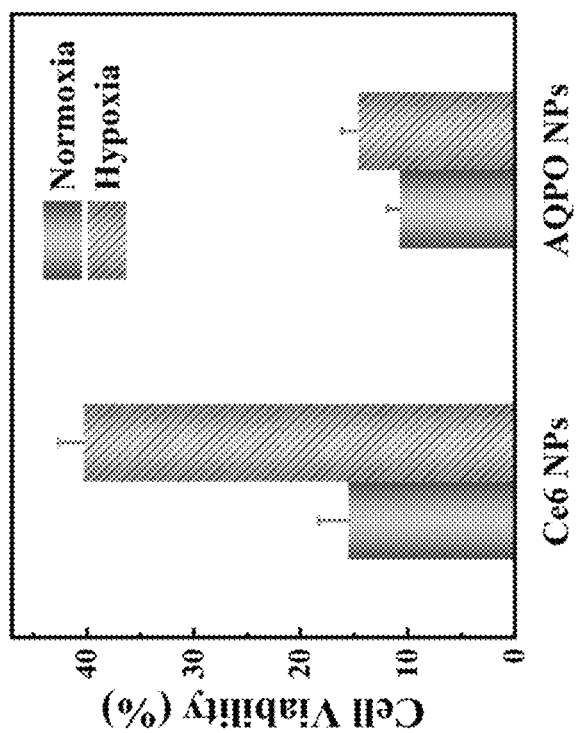
FIG. 16D shows a bar chart illustrating the comparison of photocytotoxicity to A549 cells treated with Ce6 NPs and nanoparticle of Compound A of Formula (IV) prepared in an embodiment of the present invention under normoxia and hypoxia with their corresponding maximum concentrations.

Comparative experiments were conducted using Ce6 NPs, which is a commercial PDT agent with FDA approval. As revealed in FIG. 16C, the PDT effect of the Ce6 NPs was considerably suppressed by hypoxia, which is in contrary to AQPO NPs which display a very small difference of cell viability between normoxia and hypoxia. Such a difference in photocytotoxic behaviour of the two kinds of NPs under normoxia and hypoxia was particularly prominent at their maximum concentrations (FIG. 16D).

Figure 17:
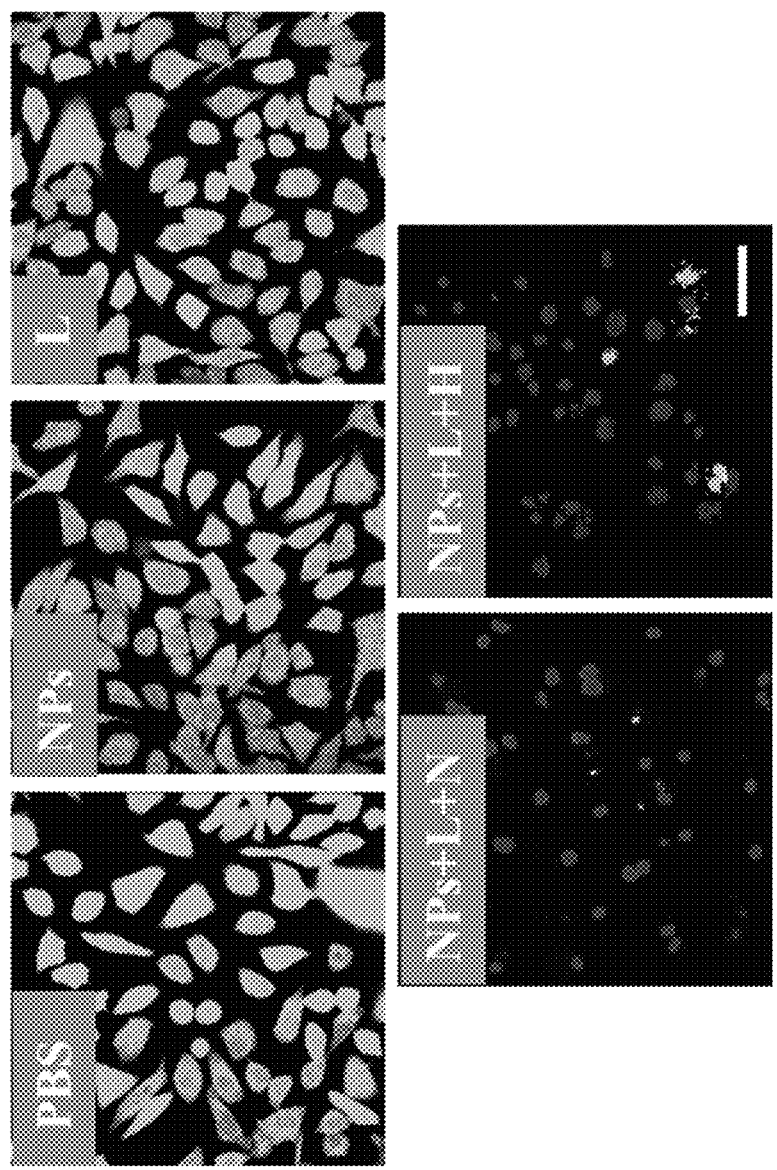
FIG. 17 shows CLSM images of A549 cells incubated with nanoparticle of Compound A of Formula (IV) prepared in an embodiment of the present invention by co-staining Calcein AM/PI after different treatments. Red fluorescence: PI; green fluorescence: Calcein-AM. N: normoxia; H: hypoxia. Scale bar=40 μm.

The photocytotoxic effect of AQPO NPs to cancer cells were further visualized using a live/dead cell co-staining viability assay (Calcein-AM/PI) by CLSM. A549 cells were seeded in 35 mm plates and cultured for 12 h. Then, the cells were incubated with 10 μg/mL of AQPO NPs for 4 h and then treated with or without white light (50 mW/cm$^2$, 5 min). After 12 h, the cells were stained with Calcein AM/PI for 30 min and then washed twice with 1×PBS. The cells treated with the same volume of 1×PBS and laser only were taken as controls. Finally, all the cell groups were imaged with CLSM. The air conditions of incubators are 21% $O_2$+5% $CO_2$ (normoxia) and 2% $O_2$+5% $CO_2$ (hypoxia), respectively. As revealed in FIG. 17, the A549 cells treated with AQPO NPs and white light were almost all dead (red fluorescence) under both normoxia and hypoxia, consistent with the MTT results.

Example 7

In Vitro PDT Evaluation of Nanoparticle of Compound a Towards Bacteria

Figure 18A:
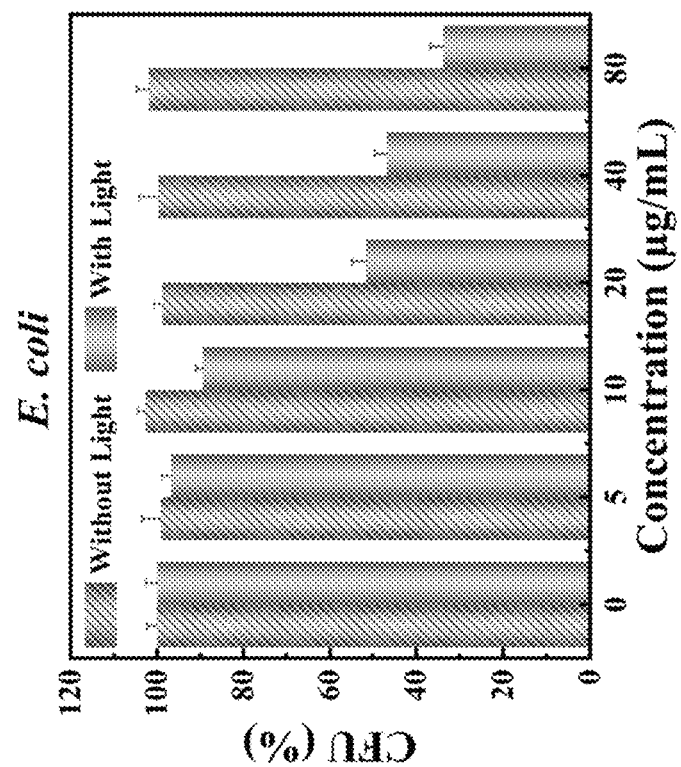
FIG. 18A shows a bar chart illustrating antibacterial activity of nanoparticle of Compound A of Formula (IV) prepared in an embodiment of the present invention towards *S. aureus*.
Figure 18B:
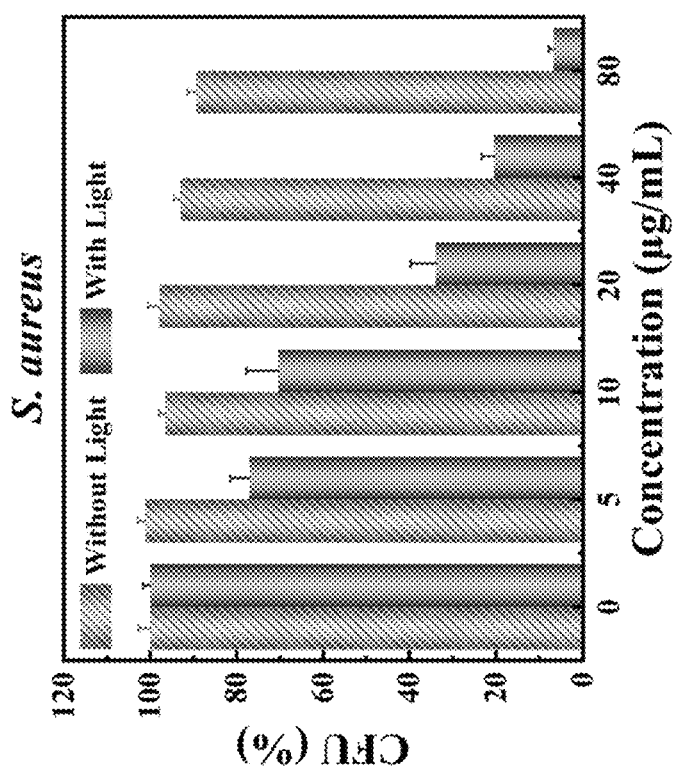
FIG. 18B shows a bar chart illustrating antibacterial activity of nanoparticle of Compound A of Formula (IV) prepared in an embodiment of the present invention towards *E. Coli*.

AQPO NPs possessed highly effective multiple-ROS generation ability. The antibacterial PDT ability of AQPO NPs was also investigated. The antibacterial activities of AQPO NPs towards Gram-positive *Staphylococcus aureus* (*S. aureus*) and Gram-negative *Escherichia coli* (*E. coli*) were examined by irradiation under white light (about 400 nm to about 700 nm). The standard plate colony-counting method was used to determine the percentage of live bacteria. Briefly, *S. aureus* and *E. coli* were harvested by centrifuging (7000 rpm for 1 min) and suspended in phosphate buffer saline (PBS, 50 mM, pH=7.4) with optical density of 1.0 at 600 nm (OD600=1.0). The resulted bacteria were incubated with AQPO NPs for 30 min in 50 mM PBS, and then were irradiated by white light for 10 min (50 mW/cm$^2$). Meanwhile, the bacteria treated without AQPO NPs or white light was used as control groups. After various treatment, the bacterial were directly diluted for 1×10$^6$ fold, and 100 μL of the diluted bacterial was spread on the solid plate for colonies formation in an incubator at 37° C. As shown in FIG. 18A and FIG. 18B, the percentage of live bacteria decreases significantly with increasing AQPO NPs concentration upon irradiation. More than 90% of *S. aureus* and 70% of *E. coli* were killed when treated with 80 μg/mL of AQPO NPs. The results indicate that AQPO NPs holds excellent antibacterial activity towards both Gram-positive and Gram-negative bacteria under irradiation. In the dark, negligible toxicity of AQPO NPs was observed when treated with *E. coli* and *S. aureus* (FIG. 18A and FIG. 18B), which strongly indicates that AQPO NPs is biocompatible.

It should be understood that the above only illustrates and describes examples whereby the present invention may be carried out, and that modifications and/or alterations may be made thereto without departing from the spirit of the invention.

It should also be understood that certain features of the invention, which are, for clarity, described in the context of separate embodiments, may also be provided in combination in a single embodiment. Conversely, various features of the invention which are, for brevity, described in the context of a single embodiment, may also be provided separately, or in any suitable subcombination.

All references specifically cited herein are hereby incorporated by reference in their entireties. However, the citation or incorporation of such a reference is not necessarily an admission as to its appropriateness, citability, and/or availability as prior art to/against the present invention.

What is claimed is:

1. A photoactive compound comprising a structure of Formula (IV):

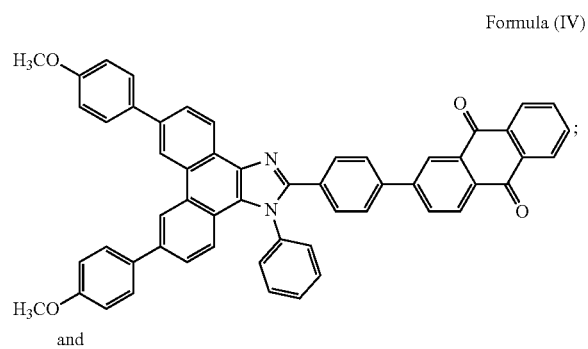

Formula (IV)

and wherein the compound is enclosed by an amphiphilic polymer to form a nanoparticle, the amphiphilic polymer comprising DSPE-PEG2000; and wherein the photoactive compound is capable of generating reactive oxygen species when it is in the form of a nanoparticle.

2. A pharmaceutical composition for photodynamically treating a tumor or infected tissue, comprising a photoactive compound having a structure of Formula (IV):

Formula (IV)

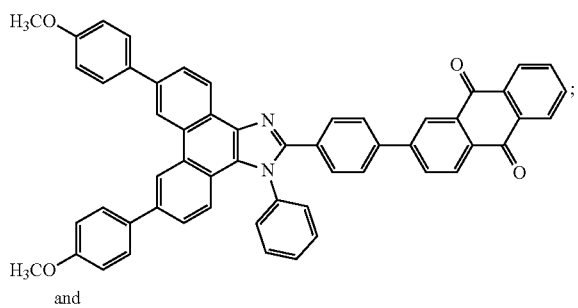

and a pharmaceutically acceptable carrier in the form of a nanoparticle enclosing the photoactive compound, the nanoparticle comprising DSPE-PEG2000; wherein the photoactive compound is capable of generating reactive oxygen species when it is in the form of a nanoparticle.

3. A method of treating a target tissue, comprising administering to a patient in need thereof a compound according to claim 1 and administering to the target tissue radiation in an amount and of a wavelength effective to activate the compound.

4. The method according to claim 3, wherein the radiation is light, and wherein the light has a wavelength within the visible spectrum.

5. The method according to claim 4, wherein the light is applied at a power intensity from about 0.5 mW/cm$^2$ to about 500 mW/cm$^2$.

6. The method according to claim 3, wherein the target tissue is a tumor.

7. The method according to claim 6, wherein the tumor is a cervical cancer, lung cancer, breast cancer, or mammary cancer.

8. The method according to claim 3, wherein the target tissue is affected by an infection.

9. A nanoparticle for photodynamically treating a target tissue that is a tumor or an infected tissue, having a core comprising a photoactive compound with a structure of Formula (IV):

Formula (IV)

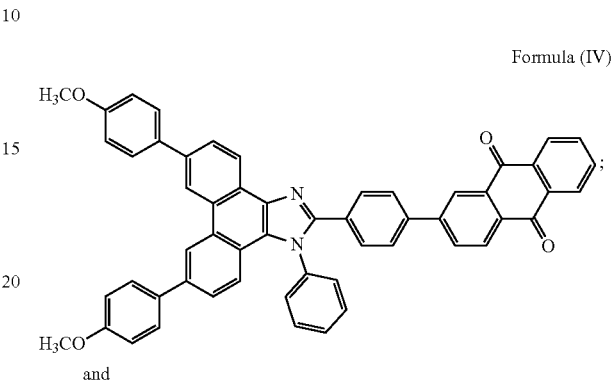

and wherein the core is enclosed by an amphiphilic polymer selected from the group consisting of DSPE-PEG2000, DSPE-PEG5000, Poloxamer 407, poly lactic-co-glycolic acid (PLGA) and a combination thereof; wherein the nanoparticle including the photoactive compound is capable of generating reactive oxygen species.

10. The nanoparticle according to claim 9, having an average particle size of about 25 nm to about 32 nm.

11. The nanoparticle according to claim 9, having an average particle size of about 29 nm.

* * * * *